(12) United States Patent
Sato et al.

(10) Patent No.: US 7,829,670 B2
(45) Date of Patent: Nov. 9, 2010

(54) PROTEINS HAVING EFFECTS OF CONTROLLING CELL MIGRATION AND CELL DEATH

(75) Inventors: Makoto Sato, Fukui (JP); Takashi Nagano, Fukui (JP)

(73) Assignee: Japan Science And Technology Agency, Saitama (JP)

( * ) Notice: Subject to any disclaimer, the term of this patent is extended or adjusted under 35 U.S.C. 154(b) by 143 days.

(21) Appl. No.: 12/037,561

(22) Filed: Feb. 26, 2008

(65) Prior Publication Data

US 2008/0275217 A1    Nov. 6, 2008

Related U.S. Application Data

(60) Division of application No. 10/788,793, filed on Feb. 27, 2004, now Pat. No. 7,498,149, which is a continuation-in-part of application No. PCT/JP02/07676, filed on Jul. 29, 2002.

(30) Foreign Application Priority Data

Aug. 27, 2001   (JP)   ............................. 2001-256910

(51) Int. Cl.
*C07K 14/00*   (2006.01)
(52) U.S. Cl. ...................... 530/350; 530/300; 435/69.1; 435/7.1; 435/6; 435/320.1
(58) Field of Classification Search .................. None
See application file for complete search history.

(56) References Cited

U.S. PATENT DOCUMENTS

| 5,599,919 A | 2/1997 | Yen et al. |
| 2003/0108554 A1 | 6/2003 | Saus et al. |

FOREIGN PATENT DOCUMENTS

WO    WO0153312    *   7/2001

OTHER PUBLICATIONS

Nagano, T. et al., "Filamin A-Interacting Protein (FLIP) Regulates Cortical Cell Migration Out of the Ventricular Zone," *Nature Cell Biology*, 4: 495-501, 2002.
Wells, Biochemistry, vol. 29, pp. 8509-8517, 1990.
Seffernick et al., J. Bacteriology, vol. 183, pp. 2405-2410, 2001.
Dyson et al. (The Journal of Cell Biology, vol. 155, No. 6, pp. 1065-1079, 2001.

* cited by examiner

*Primary Examiner*—Hope A Robinson
(74) *Attorney, Agent, or Firm*—Frommer Lawrence & Haug LLP; Thomas J. Kowalski; Smitha B. Uthaman

(57) ABSTRACT

The present invention relates to proteins which have a role in controlling neuronal cell migration and cell death as well as to the DNA which encode those proteins. It is an object of the present invention to provide control of cell migration and/or cell death by providing a method for screening for promoters or inhibitors of proteins which affect the control of cell migration and/or cell death of neurons by interacting with an actin-binding protein, Filamin 1, through promoting the degradation of Filamin 1 or the DNA encoding Filamin 1. The cDNAs of S-FILIP, L-FILIP and h-FILIP cDNAs, which interact with Filamin 1, thereby negatively affecting cell migration and cell death by promoting the degradation of the Filamin 1, were isolated and the full nucleotide and amino acid sequences thereof were determined.

3 Claims, 4 Drawing Sheets
(4 of 4 Drawing Sheet(s) Filed in Color)

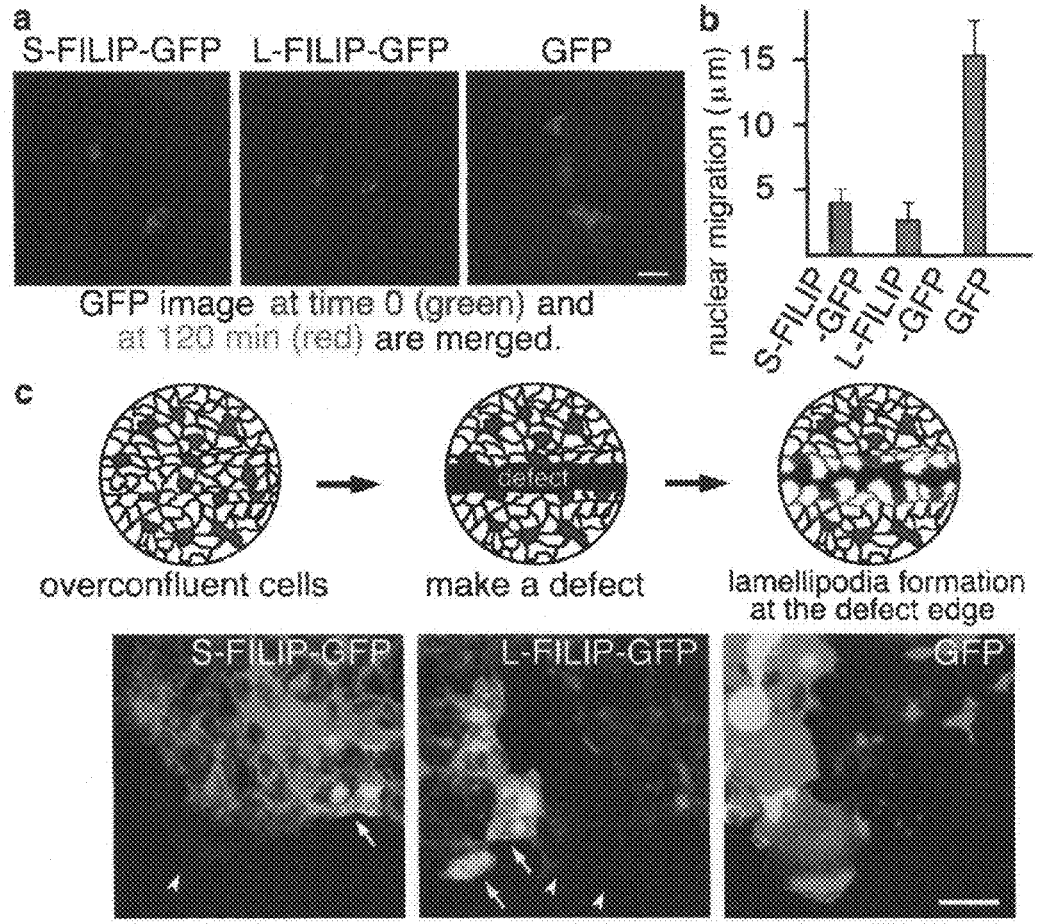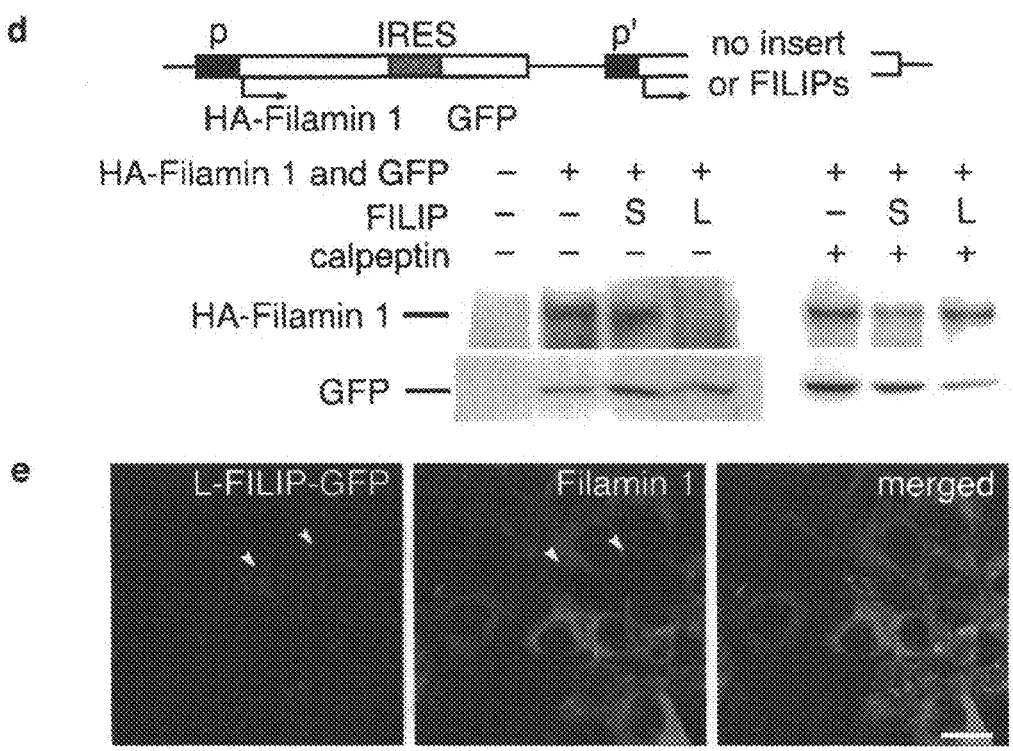
FIG 3

US 7,829,670 B2

PROTEINS HAVING EFFECTS OF CONTROLLING CELL MIGRATION AND CELL DEATH

CROSS REFERENCE TO RELATED APPLICATIONS

This application is a divisional of U.S. patent application Ser. No. 10/788,793 filed on Feb. 27, 2004 now U.S. Pat. No. 7,498,149, which is a Continuation-in-part of International Patent Application No. PCT/JP02/07676 filed Jul. 29, 2002 and published on Mar. 6, 2003 as WO 03/018804, claiming priority to Japanese application 2001-256910 filed Aug. 27, 2001. Each of the above applications, and each document cited in this text and in each of the above applications ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. patent law; e.g., they can mean "includes", "included", "including" and the like. Terms such as "consisting essentially of" and "consists essentially of" have the meaning attributed to them in U.S. patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. patent law; namely, that these terms are closed ended.

FIELD OF THE INVENTION

The present invention relates to a protein that has effects of controlling cell migration and cell death of neurons and the like, a DNA that encodes the protein, control of cell migration and/or cell death, and a method for screening a promoter or an inhibitor of the effects of controlling cell migration and/or cell death, by using the protein and the like.

BACKGROUND OF THE INVENTION

More than one hundred billion neurons exist in human brain to form complex neural circuits. Only prescribed numbers of them are formed in the adequate positions as development progresses. These neurons have very complicated shapes which never be seen in other somatic cells and extend two kinds of processes dendrite and axon from a cell body which is protoplasm including a nucleus. A dendrite comprises numerous thorn structures called spine and forms postsynaptic region that has a function for receiving information from other cells. It is known that this neuron specific shape is determined by a neuron specific actin-binding protein.

On the other hand, brain is an important organ that controls not only the action at unconsciousness level but also what is called higher-order function such as emotion, memory, learning, and creation. However, it has not revealed yet how the regions in brain are determined and how the differentiation of brains that is specific in each region are occurred. Neuronal migration is essential for construction of brain tissue, for example in cerebral cortex, a layer structure is formed by division of neural stem cells (radial glial cell) at ventricular zone and radial migration thereof with the help of the radial processes inherited in division. Although it has been indicated that molecules such as PS-NCAM or Slit are involved in these migrations of neurons, the relation has been hardly revealed yet.

As aforementioned, radial migration of postmitotic neurons is essential for neocortical development (J. Comp. Neurol. 145, 61-83, 1972, Nat. Neurosci. 4, 143-150, 2001, Nature 409, 714-720, 2001). Neurons generated in the ventricular zone have to make at least two important decisions in order to reach their destination correctly: when to start and where to stop migration. The stop of migration is thought to be regulated by Reelin (Nature 374, 719-723, 1995, Nature 389, 730-733, 1997, Nature 389, 733-737, 1997, Neuron 24, 471-479, 1999, Neuron 24, 481-489, 1999, Cell 99, 635-647, 1999, Cell 97, 689-701, 1999, Neuron 27, 33-44, 2000), however, the molecule relating to the start of migration has been poorly understood. An exception has been reported that disruption of an actin-binding protein Filamin 1 results in a human neuronal migration disorder, periventricular nodular heterotopia, in which many neurons remain lining the ventricular surface (Neuron 16, 77-87, 1996, Neuron 21, 1315-1325, 1998).

The present invention relates to a protein of the effects of controlling cell migration and cell death of such as neurons and a DNA encoding the protein, particularly, an object of the present invention is to provide a method of controlling cell migration and/or cell death and a method of screening a promoter or an inhibitor of the effects of controlling cell migration and/or cell death with the use of proteins controlling the cell motility and cell death of neurons and the DNA encoding the proteins by interacting an actin-binding protein and promoting the degradation of the actin-binding protein.

Analysis of the cerebral cortex having disorder in layer structure is thought to provide an important clue for clarification of molecular mechanism relating to neuronal migration during the development of cerebral cortex, for instance the clarification of molecular mechanism which arrests cell migration is progressing rapidly by the study of reeler mouse. Likewise, periventricular nodular heterotopia, in which immovable neurons remain at neuroepithelial layer is thought to be another clue for solving the mechanism for starting/maintaining the migration of neurons, and abnormality of an actin-binding protein Filamin 1 has been revealed to be a cause. (Though "Filamin 1" is sometimes called "Filamin A", it is indicated "Filamin 1" in the present invention.)

Meanwhile, the inventors reported about a rat nascent stage cerebral cortex-derived cytoskelton-associated novel protein FILIP (Filamin-interacting protein), it was predicted that the FILIP (S-FILIP) molecule comprised 965 amino acid residues in total, and revealed that it comprised coiled-coil structure including leucine zipper motifs at N-terminal-half of the molecule. Moreover, yeast two-hybrid screening or immuno-precipitaion analyses revealed that the C-terminal-half of FILIP molecule is combined with an actin-binding protein, Filamin 1. Filamin 1 is an essential molecule for cell migration during cerebral cortex formation period, and it is known that mutation of Filamin 1 gene causes periventricular nodular heterotopia characterized in migration disorder of cerebral cortical neuron. This led to the possibility that FILIP (S-FILIP) controls cell migration by associating with Filamin 1 to control those function at developing cerebral cortex. To verify this hypothesis, FILIP was expressed in a cultured cell and the aspect of cell migration was observed with time following. In consequence, migration of FILIP-expressing cell was controlled compared to the control, FILIP (S-FILIP) was indicated as a negative control factor of cell migration.

Subsequently, as the result of a keen study by the present inventors, FILIPs (L-FILIP and S-FILIP) were identified, FILIPs were found that they had functions for controlling cell motility and cell death, and the present invention was completed. That is, FILIP molecule (965 amino acid residues; S-FILIP; GenBank accession number D87257) (SEQ ID NOS: 3 and 4 in sequence listing) and L-FILIP which comprises 1212 residues, being constructed by adding 247 residues to molecule on the N terminal side (GenBank accession number AB055759) (SEQ ID NOS: 1 and 2 in the sequence listing).

Moreover, the result of a further study by the present inventor, human FILIP molecule (1213 amino acid residues; h-FILIP; -GenBank accession number AB086011) (SEQ ID NOS: 5 and 6 in the sequence listing), which is a human orthologue of mouse L-FILIP, was identified from human DNA library.

The present inventors found that when the novel protein L-FILIP or S-FILIP was introduced into cells, these molecules partially coexisted with filamentous-actin within the cells, and in the same cell, the degradation of filamentous-actin was yielded, it became smaller and shorter, the lamellipodia formation ratio from cell membrane was decreased, and the cell migration ratio was significantly decreased. They also found that L-FILIP which is a novel molecule had more significant Filamin 1 degradation promoting effect as well as it expressed more protein at cerebral cortex neuroepithelium than S-FILIP, from the result of investigation using cultured cells. These facts revealed that S-FILIP but L-FILIP mainly plays the role of controlling cell migration negatively by promoting degradation of Filamin 1 at cerebral cortex neuroepithelium.

When S-FILIP or L-FILIP and Filamin 1 were expressed in the same cell, the change in Filamin 1 was observed, and the degradation of Filamin 1 progressed by expression of FILIP was observed similarly as aforementioned. These changes were also significant at L-FILIP. When the expression of Filamin 1 at the brain of normal rats during their fatal stage was examined, expression of Filamin 1 gene was observed, while a number of cells were observed of which expression amount of Filamin 1 protein had largely decreased in cells localized in ventricular zone, where expression of FILIP gene being observed, and cell migration toward cortical plate having not yet occurred. On the other hand, reduction of the cell number was identified in the cultured cell to which novel molecule L-FILIP was introduced, and it was revealed that FILIPs were also related to the control of cell death. The present invention was completed based upon the knowledge mentioned above.

DESCRIPTION OF THE INVENTION

For the purposes of the present application, the term "DNA" is intended to include an isolated DNA molecule.

The present invention relates to: an isolated DNA that encodes a protein described in the following (a) or (b): (a) a protein that comprises an amino-acid sequence shown in SEQ ID NO: 2 in the sequence listing, and (b) a protein which comprises an amino-acid sequence wherein 1 or several amino acids are deleted, substituted or added in an amino-acid sequence shown in SEQ ID NO: 2 in the sequence listing, and has effects of controlling cell migration and cell death;

a DNA that comprises a base sequence shown in SEQ ID NO: 1 in the sequence listing, complementary sequence thereof, or a sequence comprising part or whole of these sequences;

a DNA that hybridizes with the DNA consisting of the gene according to paragraph 0016 in stringent condition and encodes the proteins having the effects of controlling cell migration and cell death;

a DNA that encodes the protein described in the following (a) or (b):(a) a protein that comprises an amino-acid sequence shown in SEQ ID NO: 4 in sequence listing, and (b) a protein that comprises an amino-acid sequence wherein 1 or several amino acids are deleted, substituted, or added in an amino-acid sequence shown in SEQ ID NO: 4 in the sequence listing, and has effects of controlling cell migration and cell death;

a DNA that comprises the base sequence shown in SEQ ID NO: 3 in sequence listing, complementary sequence thereof, or a sequence comprising part or whole of these sequences;

and a DNA that hybridizes with the DNA consisting of the gene according to paragraph 0019 in stringent condition and encodes the protein having the effects of controlling cell migration and cell death.

The present invention also relates to: a DNA that encodes the protein described in the following (a) or (b); (a) a protein that comprises an amino-acid sequence shown in SEQ ID NO: 6 in the sequence listing, and (b) a protein that comprises an amino-acid sequence wherein 1 or several amino acids are deleted, substituted, or added in SEQ ID NO: 6 in the sequence listing, and has effects of controlling cell migration and cell death;

a DNA that comprises the base sequence shown in SEQ ID NO: 5 in the sequence listing, complementary sequence thereof, or a sequence comprising part or whole of these sequences;

a DNA that hybridizes with the DNA consisting the gene according to paragraph 0022 in stringent condition and encodes the protein having the effects of controlling cell migration and cell death;

a protein that comprises the amino-acid sequence shown in SEQ ID NO: 2 in the sequence listing;

a protein that comprises an amino-acid sequence wherein 1 or several amino acids are deleted, substituted, or added in the amino-acid sequence shown in SEQ ID NO: 2 in the sequence listing, and has effects of controlling cell migration and cell death;

a protein that comprises the amino-acid sequence shown in SEQ ID NO: 4 in the sequence listing;

a protein that comprises an amino-acid sequence wherein 1 or several amino acids are deleted, substituted, or added in the amino-acid sequence shown in SEQ ID NO: 4 in the sequence listing, and has effects of controlling cell migration and cell death;

a protein that comprises amino-acid sequence shown in SEQ ID NO: 6 in the sequence listing;

a protein that comprises an amino-acid sequence wherein 1 or several amino acids are deleted, substituted, or added in the amino-acid sequence shown in SEQ ID NO: 6 in the sequence listing, and has effects of controlling cell migration and cell death;

the protein according to paragraph 0025, 0027, or 0029, wherein control of cell migration and cell death is caused by the degradation of Filamin 1.

The present invention further relates to: a peptide that comprises a part of the protein according to any one of paragraphs 0024 to 0030, and has effects of controlling cell migration and cell death;

the peptide according to paragraph 0031, wherein control of cell migration and cell death is caused by the degradation of Filamin 1;

a fusion protein or a fusion peptide wherein the protein according to any one of paragraphs 0024 to 0030, or the peptide according to paragraph 0031 or 0032 is bound to a marker protein and/or a peptide tag;

an antibody that specifically binds to the protein according to any one of paragraphs 0024 to 0030 or the peptide according to paragraph 0031 or 0032;

the antibody according to paragraph 0034, wherein the antibody is a monoclonal or a polyclonal antibody;

a recombinant protein or a recombinant peptide to which the antibody according to paragraph 0034 or 0035 specifically binds;

a host cell that comprises expression system which capable of expressing the protein according to any one of paragraphs 0024 to 0030 or the peptide according to paragraph 0031 or 0032;

a non-human animal whose a gene function encoding the protein according to any one of paragraphs 0024 to 0030 or the peptide according to paragraph 0031 or 0032 is deficient on its chromosome;

a non-human animal that over-expresses the protein according to any one of paragraphs 0024 to 0030 or the peptide according to paragraph 0031 or 0032;

and the non-human animal according to paragraph 0038 or 0039 which is a mouse or a rat.

The present invention still further relates to: a method for screening an inhibitor or a promoter of effects of controlling cell migration and/or cell death, wherein the protein according to any one of paragraphs 0024 to 0030, the peptide according to paragraph 0031 or 0032, or a cell membrane expressing the protein according to any one of paragraphs 0024 to 0030 or the peptide according to paragraph 0031 or 0032, and a test substance are used;

a method for screening an inhibitor or a promoter of effects of controlling cell migration and/or cell death, or an inhibitor or a promoter of the expression of the protein according to any one of paragraphs 0024 to 0030 or of the peptide according to paragraph 0031 or 0032, wherein a cell expressing the protein according to any one of paragraphs 0024 to 0030 or the peptide according to paragraph 0031 or 0032, and a test substance are used;

and a method for screening an inhibitor or a promoter of effects of controlling cell migration and/or cell death, or an inhibitor or a promoter of the expression of the protein to any one of paragraphs 0024 to 0030 or the peptide according to paragraph 0031 or 0032, wherein the non-human animal according to any one of paragraphs 0038 to 0040 and a test substance are used.

The present invention also relates to: the promoter of effects of controlling cell migration and cell death obtained by the method for screening according to any one of paragraphs 0041 to 0043;

the inhibitor of effects of controlling cell migration and cell death obtained by the method for screening according to any one of paragraphs 0041 to 0043;

a promoter of the expression of the protein according to any one of paragraphs 0024 to 0030 or of the peptide according to paragraph 0031 or 0032, being obtained by the method for screening according to any one of paragraphs 0041 to 0043;

an inhibitor of the expression of the protein according to any one of paragraphs 0024 to 0030 or of the peptide according to paragraph 0031 or 0032, being obtained by the method for screening according to any one of paragraphs 0041 to 0043;

the inhibitor of metastasis of a cancer/a tumor, or a regulant of cell migration for transplantation treatment that includes the protein according to any one of paragraphs 0024 to 0030, the peptide according to paragraph 0031 or 0032, the recombinant protein or the recombinant peptide according to paragraph 0036, the antibody according to paragraph 0034 or 0035, the inhibitor of effects of controlling cell migration and cell death according to paragraph 0045, or the inhibitor of the expression according to paragraph 0047 as an active ingredient.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 is a photograph showing the results of degradation of Filamin 1 by L-FILIP or S-FILIP of the present invention and reduction of cell motility thereby.

BEST MODE FOR CARRYING OUT THE INVENTION

Figure 1:
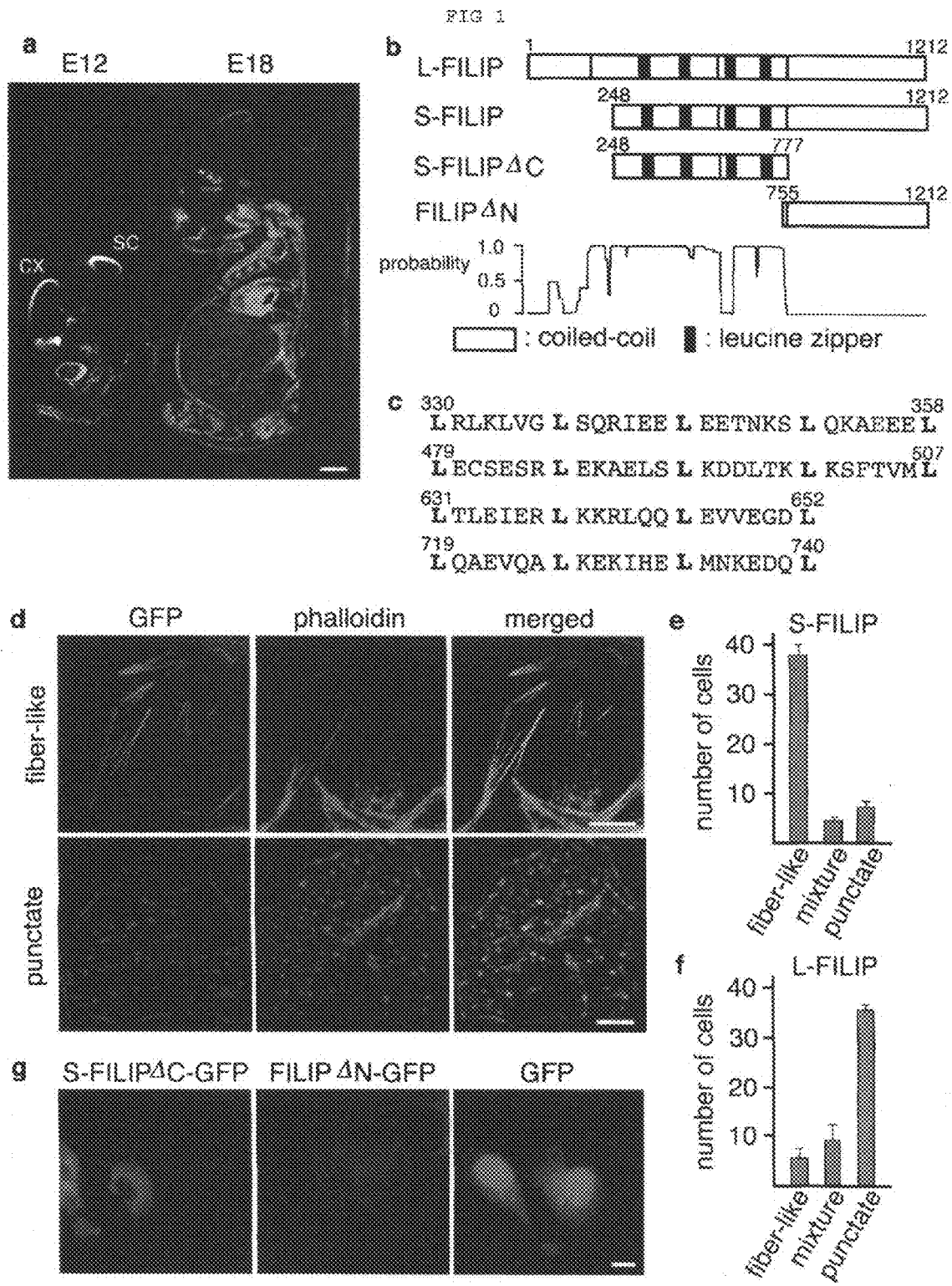
FIG. 1 is a photograph showing the localization of L-FILIP cDNA or S-FILIP cDNA of the present invention and the structure of FILIPs.

As a protein according to the present invention, a protein that comprises an amino-acid in which one or several amino acids are deleted, substituted or added, and has effects of controlling cell migration and cell death in L-FILIP shown in SEQ ID NO: 2, S-FILIP shown in SEQ ID NO: 4, or an amino-acid sequence shown in SEQ ID NO: 2 OR 4 is exemplified. Aforementioned effects of controlling cell migration and cell death are effects of controlling cell motility and cell death. The protein can be prepared by known methods on the basis of its DNA sequence information etc., and its derivation is not limited specifically. A Peptide being an object of the present invention is not particularly limited as long as it is a peptide that consists of a part of a protein of the present invention and has effects of controlling cell migration and cell death. Aforementioned protein and peptide being an object of the present invention, and recombinant protein and peptide to which the antibody, which specifically binds to these proteins and peptides, specifically binds, may be generically called hereinafter as "the proteins/peptides of the present invention". Meanwhile, the proteins/peptides of the present invention can be prepared by known method on the basis of its DNA sequence information etc., and its derivation is not particularly limited to rat.

An antibody that "specifically binds" to a protein is one that binds to a protein, but which does not recognize and bind to other molecules in a sample, e.g., a biological sample, which naturally includes the protein.

As a DNA being an object of the present invention, any DNA can be used as long as it encodes the aforementioned protein of the present invention, for instance, a DNA encoding L-FILIP shown in SEQ ID NO: 2 in the sequence listing, a DNA encoding S-FILIP shown in SEQ ID NO: 4 in the sequence listing and a protein comprising an amino-acid in which one or several amino acids are deleted, substituted or added in SEQ ID NO: 2 or 4 in the sequence listing, and having effects of controlling cell migration and cell death or an amino-acid sequence shown or a DNA comprising base sequence shown in SEQ ID NO: 1 or 3 in the sequence listing, its complementary sequence, and part or whole of these sequences, are exemplified specifically. These can be prepared by known method on the basis of its DNA sequence information etc., for example, from gene library or cDNA library of human, mouse, rat, rabbit, and the like.

Also contemplated by the present invention are proteins or peptides which are at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% homologous to any of SEQ ID NOS: 2, 4, and 6.

A DNA that encodes the novel protein comprising effects of controlling cell migration and cell death can also be obtained by performing hybridization with the DNA comprising base sequence shown in SEQ ID NO: 1 or 3 in the sequence listing, its complemented sequence, and part the whole of these sequences as a probe in stringent condition to various DNA libraries and isolating the DNA hybridizing with the probe. The DNA obtained in this manner is also within the scope of the present invention. As a hybridization condition for obtaining the DNA of the present invention, hybridization at 42° C. and rinse at 42° C. with buffer including 1×SSC and 0.1% SDS, more preferably hybridization at 65° C. and rinse at 65° C. with buffer including 0.1×SSC and 0.1% SDS is exemplified. Although, factors that influence on the stringency of hybridization include various factors other than above-mentioned temperature condition, those skills in the art can achieve stringency equivalent to the stringency of above-mentioned hybridization by combining various factors properly.

Also contemplated by the present invention are DNA sequences or fragments which are at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% homologous to any of SEQ ID NOS: 1, 3, or 5.

Sequence identity with respect to any of the sequences presented here can be determined by a simple "eyeball" comparison (i.e. a strict comparison) of any one or more of the sequences with another sequence to see if that other sequence has, for example, at least 70% sequence identity to the sequence(s).

Alternatively, relative sequence identity can also be determined by commercially available computer programs that can calculate % identity between two or more sequences using any suitable algorithm for determining identity, using for example default parameters. A typical example of such a computer program is CLUSTAL. Other computer program methods to determine identify and similarity between the two sequences include but are not limited to the GCG program package (Devereux et al 1984 Nucleic Acids Research 12: 387) and FASTA (Atschul et al 1990 J Molec Biol 403-410).

The sequence identity or percent homology for proteins and nucleic acids can also be calculated as $(N_{ref} - N_{dif}) \times 100 / N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}=2$ and $N_{ref}=8$).

Percent homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST™ package (Ausubel et al., 1999 ibid—Chapter 18), FASTA (Atschul et al., 1990, J. Mol. Biol., 403-410) and the GENEWORKS™ suite of comparison tools. Both BLAST™ and FASTA are available for offline and online searching (Ausubel et al., 1999 ibid, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST™ suite of programs. GCG Wisconsin programs generally use either the public default values or a custom symbol comparison table if supplied. It is preferred to use the public default values for the GCG package, or in the case of other software, the default matrix, such as BLOSUM62.

Advantageously, the BLAST™ algorithm is employed, with parameters set to default values. The BLAST™ algorithm is described in detail at the National Center for Biotechnology Information website, which is incorporated herein by reference. The search parameters are defined as follows, can be advantageously set to the defined default parameters.

Advantageously, "substantial identity" when assessed by BLAST™ equates to sequences which match with an EXPECT value of at least about 7, preferably at least about 9 and most preferably 10 or more. The default threshold for EXPECT in BLAST™ searching is usually 10.

BLAST™ (Basic Local Alignment Search Tool) is the heuristic search algorithm employed by the programs blastp, blastn, blastx, tblastn, and tblastx; these programs ascribe significance to their findings using the statistical methods of Karlin and Altschul (Karlin and Altschul 1990, Proc. Natl. Acad. Sci. USA 87:2264-68; Karlin and Altschul, 1993, Proc. Natl. Acad. Sci. USA 90:5873-7; see the National Center for Biotechnology Information website) with a few enhancements. The BLAST™ programs are tailored for sequence similarity searching, for example to identify homologues to a query sequence. For a discussion of basic issues in similarity searching of sequence databases, see Altschul et al (1994) Nature Genetics 6:119-129.

The five BLAST™ programs available at the National Center for Biotechnology Information website perform the following tasks: blastp—compares an amino acid query sequence against a protein sequence database; blastn—compares a nucleotide query sequence against a nucleotide sequence database; blastx—compares the six-frame conceptual translation products of a nucleotide query sequence (both strands) against a protein sequence database; tblastn—compares a protein query sequence against a nucleotide sequence database dynamically translated in all six reading frames (both strands); tblastx—compares the six-frame translations of a nucleotide query sequence against the six-frame translations of a nucleotide sequence database.

BLAST™ uses the following search parameters:

HISTOGRAM—Display a histogram of scores for each search; default is yes. (See parameter H in the BLAST™ Manual).

DESCRIPTIONS—Restricts the number of short descriptions of matching sequences reported to the number specified; default limit is 100 descriptions. (See parameter V in the manual page).

EXPECT—The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST™ Manual).

CUTOFF—Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST™ Manual). Typically, significance thresholds can be more intuitively managed using EXPECT.

ALIGNMENTS—Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST™ Manual).

MATRIX—Specify an alternate scoring matrix for BLASTP, BLASTX, TBLASTN and TBLASTX. The default matrix is BLOSUM62 (Henikoff & Henikoff, 1992). The valid alternative choices include: PAM40, PAM120, PAM250 and IDENTITY. No alternate scoring matrices are available for BLASTN; specifying the MATRIX directive in BLASTN requests returns an error response.

STRAND—Restrict a TBLASTN search to just the top or bottom strand of the database sequences; or restrict a BLASTN, BLASTX or TBLASTX search to just reading frames on the top or bottom strand of the query sequence.

FILTER—Mask off segments of the query sequence that have low compositional complexity, as determined by the SEG program of Wootton & Federhen (1993) Computers and Chemistry 17:149-163, or segments consisting of short-periodicity internal repeats, as determined by the XN U program of Claverie & States (1993) Computers and Chemistry 17:191-201, or, for BLASTN, by the DUST program of Tatusov and Lipman (see the National Center for Biotechnology Information website). Filtering can eliminate statistically significant but biologically uninteresting reports from the blast output (e.g., hits against common acidic-, basic- or proline-rich regions), leaving the more biologically interesting regions of the query sequence available for specific matching against database sequences.

Low complexity sequence found by a filter program is substituted using the letter "N" in nucleotide sequence (e.g., "NNNNNNNNNNNNN") and the letter "X" in protein sequences (e.g., "XXXXXXXXX").

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect. Furthermore, in some cases, sequences are masked in their entirety, indicating that the statistical significance of any matches reported against the unfiltered query sequence should be suspect.

NCBI-gi—Causes NCBI gi identifiers to be shown in the output, in addition to the accession and/or locus name.

Most preferably, sequence comparisons are conducted using the simple BLAST™ search algorithm provided at the National Center for Biotechnology Information website. In some embodiments of the present invention, no gap penalties are used when determining sequence identity.

As a fusion protein and a fusion peptide of the present invention, any fusion protein and fusion peptide can be used as long as the proteins/peptides of the present invention is bound to marker protein and/or peptide tag. A marker protein is not particularly limited as long as it is a marker protein conventionally known, alkaline phosphatase, Fc region of antibodies, HRP, GFP, and the like are exemplified as specific examples. Further, as a peptide tag of the present invention, a peptide tag conventionally known such as HA tag, Myc tag, His tag, FLAG™ tag, and GST tag are specifically exemplified. The fusion protein can be prepared by known methods. It is useful in purification of the protein and the like having effects of controlling cell migration and cell death by utilizing affinity of Ni-NTA and His tag, in detection of protein having effects of controlling cell migration and cell death, and in quantification of antibodies directed against a protein having effects of controlling cell migration and cell death. It is also useful as an inhibitor of cancer and tumor metastasis or a regulant of cell migration for transplantation therapy, and a reagent for research in the field concerned.

As an antibody that binds specifically to the proteins or peptides of the present invention, an immunity-specific antibody such as monoclonal antibody, polyclonal antibody, chimeric antibody, single-stranded antibody, and humanized antibody are exemplified as specific examples, where these antibodies can be prepared by known methods using the whole or a part of the above-mentioned proteins/peptides of the present invention, fusion protein, fusion peptide, and the like as an antigen, and monoclonal antibody is more preferable among them in view of specificity. The antibody such as monoclonal antibody is useful, for instance not only as an inhibitor of cancer and tumor metastasis or a regulant of cell migration for transplantation therapy, but also in clarifying the mechanism of such as cancer and tumor metastasis and cell migration of neuron and the like.

The aforementioned antibody of the present invention is produced by administering the proteins/peptides of the present invention, a fragment thereof containing epitope, or a cell expressing the protein on the surface of its membrane to an animal (preferably other than human) with the use of conventional protocol, for example, the monoclonal antibody can be prepared by an arbitrary method which brings antibodies developed by cultured materials of continuous cell line, such as hybridoma method (Nature 256, 495-497, 1975), trioma method, human B cell hybridoma method (Immunology Today 4, 72, 1983), and EBV-hybridoma method (MONOCLONAL ANTIBODIES AND CANCER THERAPY, pp. 77-96, Alan R. Liss, Inc., 1985) can be used.

A preparation method of single-stranded antibody (U.S. Pat. No. 4,946,778) can be applied in order to the preparation of single-stranded antibody against the above-mentioned proteins/peptides of the present invention. Further, a humanized antibody can be expressed by using a transgenic mouse or other mammal, a clone expressing the proteins/peptides of the present invention can be isolated/identified with the above-mentioned antibody, or the polypeptide can be purified with affinity chromatography. The antibodies against the proteins/peptides of the present invention may be used usefully as an inhibitor of cancer and tumor metastasis or a regulant of cell migration for transplantation therapy, and may also be used usefully in clarifying the mechanism of such as cancer and tumor metastasis and cell migration of neuron and the like, as aforementioned. Further, the recombinant protein or peptide to which these antibodies specifically bind are also included in the proteins/peptides of the present invention as aforementioned.

Functions of the proteins/peptides of the present invention can be analyzed by using, for example, antibodies such as the aforementioned monoclonal antibodies and the like that are labeled with fluorescent materials such as FITC (Fluorescein isothiocyanate), tetramethylrhodamine isothiocyanate, etc., radioisotopes such as $^{125}I$, $^{32}P$, $^{14}C$, $^{35}S$, $^{3}H$, etc. or enzymes such as alkaline phosphatase, peroxidase, β-galactosidase, phycoerythrin, etc. and by using fusion proteins fused with fluorescence proteins such as Green Fluorescent Protein (GFP) etc. As for immunological detection methods using the antibodies of the present invention, RIA method, ELISA method, fluorescent-antibody method, plaque method, spot method, hemagglutination, Ouchterlony method, etc. are exemplified.

The present invention also relates to a host cell comprising an expression system, which is able to express the proteins/peptides of the present invention. Introduction of a gene that encodes the proteins/peptides of the present invention into a host cell can be performed by the method written in a number of standard laboratory manuals such as of Davis et al. (BASIC METHODS IN MOLECULAR BIOLOGY, 1986), and of Sambrook et al. (MOLECULAR CLONING: A LABORATORY MANUAL, $2^{nd}$ Ed., Cold Spring Harbor Laboratory Press, Cold Spring Harbor, N.Y., 1989), for example, calcium phosphate transfection, DEAE-dextran-mediated transfection, transvection, microinjection, cationic lipid-mediated transfention, electroporation, transduction, scrape loading, ballistic introduction, and infection. As a host cell; bacterial procaryotic cell, such as *Escherichia coli, Streptomyces, Bucillus subtilis, Streptococcus*, and *Staphylococcus*; fungal cell, such as yeast and *Aspergillus*; insect cell, such as *Drosophila* S2 and *Spodoptera* Sf9; animal cell, such as L cell, CHO cell, COS cell, NIH3T3 cell, HeLa cell, C127 cell, BALB/c3T3 cell (including a mutant strain deficient in dihydrofolate reductase or thymidine kinase), BHK21 cell, HEK293 cell, and Bowes malignant melanoma cell; and plant cell can be exemplified.

As an expression system, any expression system can be used as long as it is an expression system that can express the proteins/peptides of the present invention in a host cell, an expression system derived from chromosome, episome, mammal, or virus, for example; a vector derived from bacterial plasmid, yeast plasmid, papova virus such as SV40, vaccinia virus, adenoviirus, fowl poxvirus, pseudorabies virus, retrovirus; a vector derived from bacteriophage, transposon, or combination of these vectors, for example a vector derived from genetic component of plasmid and bacteriophage such as cosmid or phagemid can be exemplified as a specific examples. The expression system may not only yield expression but also include a regulatory sequence for controlling expression.

A host cell comprising the aforementioned expression system, a cell membrane of the cell, and the proteins/peptides of the present invention obtained by culture of the cell can be used for a method for screening the present invention as described below. For example, as the method for obtaining cell membrane, the method by F. Pietri-Rouxel et al. (Eur. J. Biochem., 247, 1174-1179, 1997) and the like can be used. For recovering and purifying the proteins/peptides of the present invention from cell culture, the known methods including ammonium sulfate—or ethanol precipitation, acid extraction, anion or cation exchange chromatography, phosphocellulose chromatography, hydrophobic interaction chromatography, affinity chromatography, hydroxyapatite chromatography, and lectin chromatography, preferably, high-performance liquid chromatography is used. As a column especially used for affinity chromatography, columns to which antibodies to the proteins/peptides of the present invention are bound, for instance, are used and when ordinary peptide tags are added to the proteins/peptides of the present invention mentioned above, columns to which substances having affinity with the peptide tags are bound are used in order to obtain the proteins/peptides of the present invention. The method for purifying the proteins/peptides of the present invention can also be applied for peptide synthesis.

In the present invention, a non-human animal whose gene function to encode the proteins/peptides of the present invention mentioned above is deficient on its chromosome means a non-human animal part or whole of whose gene on its chromosome encoding the proteins/peptides of the present invention is inactivated by gene mutation such as destruction, deletion, substitution, etc. do that whose function to express the proteins/peptides the present invention is lost. Further, a non-human animal which over-expresses the proteins/peptides of the present invention is specifically exemplified by a non-human animal which produces larger amount of the proteins/peptides of the present invention than a wild-type non-human animal does. Although rodents or the like such as mice, rats, etc. are particularly exemplified for non-human animals of the present invention, the examples will not be limited to these animals only.

Homozygous non-human animals that are born according to Mendel's Law include a deficient type or the over-expressing type for the proteins/peptides of the present invention, as well as their wild-type littermates. By using the deficient type animals or the over-expressing type animals of these homozygous non-human animals together with their wild-type littermate at the same time, accurate comparative experiments can be carried out on the individual level. In performing screening of the present invention described below, it is, therefore preferable to use the wild type non-human animals, i.e. animals of the same species as or even better the littermates of, non-human animals whose gene function to encode the proteins/peptides of the present invention is deficient or over-expressing on their chromosomes with a combination of the deficient or over-expressing type animals. The method of producing a non-human animal whose function to encode the proteins/peptides of the present invention is deficient or over-expressing on its chromosome is now explained in the following with an L-FILIP knockout mouse and an L-FILIP transgenic mouse as examples.

A mouse, for instance, whose gene function to encode the L-FILIP protein is deficient on its chromosome, i.e. an L-FILIP knockout mouse is generated by the following steps. A gene encoding mouse L-FILIP, which is homologous to rat L-FILIP, is screened by using a gene fragment obtained by a method such as PCR or the like from the mouse gene library. A screened gene which encodes mouse L-FILIP is subcloned with a viral vector or the like and is then identified by DNA sequencing. The whole or part of a gene of this clone which encodes mouse L-FILIP is substituted with a pMC1 neo gene cassette or the like. A gene such as a diphtheria toxin A fragment (DT-A) gene, a herpes simplex virus thymidine kinase (HSV-tk) gene, etc. is introduced onto the 3'-end, and thus a targeting vector is constructed.

The targeting vectors thus constructed are linearized and introduced into ES cells by electroporation or the like to cause homologous recombination. Among the homologous recombinants, ES cells in which homologous recombination have occurred are selected by the use of antibiotics such as G418, ganciclovir (GANC), etc. It is preferable to confirm whether the ES cells selected are the recombinants of the interest by Southern blotting or the like. A clone of the ES cells confirmed is microinjected into a mouse blastocyst, and which blastocyst is placed back to the recipient mouse to generate a chimeric mouse. A heterozygous mouse can be obtained by intercrossing the chimeric mouse with a wild-type mouse. By further intercrossing the heterozygous mice, the L-FILIP knockout mice of the present invention can be generated. Whether the ability of expressing L-FILIP is lost in an L-FILIP knockout mouse is examined by Northern blotting upon isolating RNA from the mouse obtained by the above-described method and Western blotting or the like with which the L-FILIP expression in the mouse can be directly examined.

An L-FILIP transgenic mouse is created by following steps. A promoter such as chicken β-actin, mouse neurofilament, SV40, etc. and poly (A) such as rabbit β-globin SV40, etc. or introns are fused with cDNA encoding L-FILIP derived from human, mouse, rat, rabbit, etc., to construct a transgene. This transgene is microinjected into the pronuclear of mouse fertilized egg. After the obtained egg cell is cultured, it is transplanted to the oviduct of the recipient mouse which was fed thereafter. Neonatal mice that have the aforementioned cDNA were selected from among all the mice born and thus the transgenic mice are created. Neonatal mice having the cDNA can be selected by extracting crude DNA from the mice tails or the like and then by a dot hybridization method using a gene encoding the introduced L-FILIP as a probe and by PCR method or the like using a specific primer.

The host cell that comprises: the gene or DNA which encodes the above-mentioned proteins/peptides of the present invention; the proteins/peptides of the present invention; the fusion protein of the proteins/peptides of the present invention combined with marker protein and/or peptide tag; antibodies against the proteins/peptides of the present invention; and an expression system which is able to express the proteins/peptide of the present invention is useful for an inhibitor for metastasis of a cancer or a tumor or a regulant of cell migration for transplantation treatment as described below specifically. It is also available for elucidation of mechanisms such as metastasis of a cancer or a tumor or cell migration of neuron and the like as well as control of cell migration and/or cell death, a method for screening an inhibitor or a promoter of effects of controlling cell migration and/or cell death, or a method for screening an inhibitor or a promoter for expressing the proteins/peptides of the present invention.

As the method for screening an inhibitor or a promoter for controlling cell migration and/or cell death of the present invention: a method using the above-mentioned proteins/peptides of the present invention or a cell membrane expressing the proteins/peptides of the present invention, and a test substance, a method using a cell membrane expressing the above-mentioned proteins/peptides of the present invention and a test substance, a method using non-human animal such as knockout mouse or transgenic mouse of the proteins/peptides of the present invention and a test substance, and others are exemplified. Further, a method using a cell membrane expressing the above-mentioned proteins/peptides of the present invention and a test substance, a method using non-human animal such as knockout mouse or transgenic mouse of the proteins/peptides of the present invention and a test substance, and others can be used for a method for screening an inhibitor or a promoter for expressing the proteins/peptides of the present invention.

As the method for screening that uses the above-mentioned proteins/peptides of the present invention or a cell membrane expressing the proteins/peptides of the present invention and a test substance, a method of measuring and evaluating effects of controlling cell migration and cell death of the proteins/peptides of the present invention, by contacting the proteins/peptides or the proteins/peptides expressing on the surface of cell membrane with a test substance can be specifically exemplified. As the method for screening that uses a cell expressing the proteins/peptides of the present invention and a test substance, a method of measuring and evaluating effects of controlling cell migration and cell death of the proteins/peptides of the present invention, or the variation of expression amounts of the proteins/peptides of the present invention, by contacting a cell expressing the proteins/peptides of the present invention with a test substance can be specifically exemplified.

As the method for screening that uses non-human animal whose function of gene for encoding above-mentioned protein and peptide of the present invention is deficient on the chromosome or non-human animal which over-expresses the proteins/peptides of the present invention and a test substance, a method for measuring and evaluating the effects of controlling cell migration and cell death of the proteins/peptides of the present invention or the variation in expression amounts of the proteins/peptides of the present invention by contacting the cell or the tissue obtained from these non-human animal with a test substance in vitro, a method for measuring and evaluating the effects of controlling the cell migration and cell death of the proteins/peptides of the present invention or the variation in expression amounts of the proteins/peptides of the present invention at the cell or the tissue obtained from these non-human animal after administering a test substance in advance to the non-human animal whose function of gene for encoding the proteins/peptides of the present invention is deficient on the chromosome or non-human animal which over-expresses the proteins/peptides of the present invention, a method for measuring and evaluating effects of controlling cell migration and cell death of the proteins/peptides of the present invention or the variation in expression amounts of the proteins/peptides of the present invention at the non-human animal after administering a test substance in advance to the non-human animal whose function of gene for encoding the proteins/peptides of the present invention is deficient on the chromosome or non-human animal which over-expresses the proteins/peptides of the present invention, and etc., are specifically exemplified.

The promoter of effects of controlling cell migration and cell death or the promoter of expression of the present invention obtained from the screening method mentioned above can be used for such as treatment of patients requiring promotion of effects of controlling cell migration and cell death, or promotion of expression of the proteins/peptides of the present invention. The inhibitor of effects of controlling cell migration and cell death or the expression inhibitor of the present invention obtained from the screening method mentioned above can be used for such as treatment of patients requiring inhibition of effects of controlling cell migration and cell death, or inhibition of expression of the proteins/peptides of the present invention. The proteins/peptides of the present invention or the antibody against it can be used as an active ingredient for an inhibitor of cancer and tumor metastasis or a regulant of cell migration for transplantation therapy, and the like. It can be used missile therapy, as well.

The active ingredient(s) of a pharmaceutical composition is contemplated to exhibit excellent therapeutic activity, for example, in the treatment of cancer. Dosage regimes may be adjusted to provide the optimum therapeutic response. For example, several divided doses may be administered daily or the dose may be proportionally reduced as indicated by the exigencies of the therapeutic situation. Dosages may be administered at intervals of the course of several days, weeks, months or years.

The active compound may be administered in a convenient manner such as by the oral, intravenous (where water soluble), intramuscular, subcutaneous, intranasal, intradermal or suppository routes or implanting (e.g. using slow release molecules). The method of administration may depend on factors such as the location of the cancer or other ailment in the body which is to be treated. Depending on the route of administration, the active ingredient may be required to be coated in a material to protect said ingredients from the action of enzymes, acids and other natural conditions which may inactivate said ingredient.

In order to administer the combination by other than parenteral administration, it will be coated by, or administered with, a material to prevent its inactivation. For example, the combination may be administered in an adjuvant, co-administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin.

Liposomes include water-in-oil-in-water CGF emulsions as well as conventional liposomes.

The active compound may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of superfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilisation. Generally, dispersions are prepared by incorporating the sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the combination of polypeptides is suitably protected as described above, it may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. The amount of active compound in such therapeutically useful compositions in such that a suitable dosage will be obtained.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms are dictated by and directly dependent on (a) the unique characteristics of the active material and the particular therapeutic effect to be achieved, and (b) the limitations inherent in the art of compounding such as active material for the treatment of disease in living subjects having a diseased condition in which bodily health is impaired.

Acceptable carriers or diluents for therapeutic use are well known in the pharmaceutical art, and are described, for example, in Remington's Pharmaceutical Sciences, Mack Publishing Co. (A. R. Gennaro edit. 1985).

The principal active ingredients are compounded for convenient and effective administration in effective amounts with a suitable pharmaceutically acceptable carrier in dosage unit form. In the case of compositions containing supplementary active ingredients, the dosages are determined by reference to the usual dose and manner of administration of the said ingredients.

For example, in one aspect these therapeutic agents can be administered orally or parenterally. Pharmaceutical solid such as powders, granule, capsules, and tablets or pharmaceutical liquid such as syrup or elixir can be an oral administration agent, or can be an injection, a percutaneous preparation, suppository, or the like as a parenteral administration agent. These formulations can be produced in a usual manner by adding an auxiliary agent admitted pharmacologically and pharmaceutical technologically to active constituents. For example, components of formulation of diluents such as light silicic acid anhydride, starch, lactose, crystalline cellulose, and lactose calcium, disintegrator such as carboxy methyl cellulose and of lubricant such as magnesium stearate for oral agent and muscal administration agent, components of formulation of solubilizer or auxiliary solubilizer such as saline, mannitol, and propylene glycol, and of suspension such as surface active agent for injection, and further components of formulation of solubilizer or auxiliary solubilizer of water or oil-based and of adhesive for external preparation are used as an auxiliary agent.

Applied dose can be determined properly depending on the kind of objective disease, age, gender, body weight, and symptom of patient and administration pattern.

Depending upon the need, the complex(es) may be administered at a dose of from about 0.001 to about 30 mg/kg body weight, such as from about 0.1 to about 10 mg/kg, or from about 0.1 to about 1 mg/kg body weight.

Of course, for any composition to be administered to an animal or human, and for any particular method of administration, it is preferred to determine therefore: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein.

The present invention will be explained more specifically with examples below, but the scope of the present invention is not limited to these examples. In the following example, Wister rats (Keari; SLC) which were housed with food and water ad libitum under a constant temperature and humidity were used. For the animal mentioned above, embryonic day 0 (E0) is defined as the day of confirmation of the vaginal plug and day of birth is designated as P0 (postnatal day 0). Rats of P0 to P7 were anesthetized by hypothermia, while Rats of P14 to adults including being pregnant were anesthetized by intraperitoneal injection of sodium pentobarbital at 40 mg/kg.

Example 1

Isolation of FILIP cDNA and Localization of FILIP

Although it has been known that Filamin 1 (ABP-280), an actin binding protein, is an essential component of the radial migratory machinery for obtaining postmitotic neocortical neurons (Neuron 21, 1315-1325, 1998), its expression in migratory and postmigratory neurons involved in the development of neocortex, in the region from the intermediate zone to the cortical plate (Neuron 21, 1315-1325, 1998), suggests that the start of migration out of the ventricular zone is possibly controlled by other system. In order to elucidate the molecules concerning controlling the start of neuronal migration, mRNA differential display, in situ hybridization histochemistry, and screening of rat cDNA library were conducted according to the method written in Mol. Brain. Res. 62, 187-195, 1998. First, genes that expressed more abundantly in the neocortics of Wistar rats on embryonic day 11 to 12 (E11 to 12) compared with Wistar rats on embryonic day 18 to 20 (E18 to 20) were isolated by mRNA differential display. Postmitotic neurons were at the stage of migrating out of the ventricular zone toward the pial surface on E12 Wistar rats, whereas most of them had already left there at around E18 to 20 by which neurogenesis was complete. The two hundred gene fragments obtained from the results above, which expressed dramatically on E12 but not so much on E18 to 20 were sequenced and 80 independent clones were obtained by excluding overlaps.

Then, further selection was performed by in situ hybridization histochemistry with a part of the full-length of rat S-FILIP (165 nucleotides; base sequence 1289-1453) as a probe. Consequently, among 80 independent clones, one novel clone showing expression in the ventricular zone of the cortex was isolated, which was named filip (Filamin-interacting protein). In order to investigate expression of the FILIP (S-FILIP) gene, in situ hybridization for rats E12 and 18 was performed with its sagittal section. The results were shown in FIG. 1a. According to this, positive signal was confirmed at ventricular zone of cortex (cx) and superior colliculus (sc) in central nervous system of E12 (FIG. 1a left). The signal could not been confirmed abundantly at ventricular zone of E18, however, they were confirmed abundantly at heart, aorta, gastrointestinal tract, and diaphragm, and filip gene was found that they expressed at myocardium, skeletal muscle, and smooth muscle (FIG. 1a right). The scale bar in FIG. 1a shows 1 mm.

cDNA library derived from frontal cortex of a Wistar rat E11 was constructed and screened FILIP with the probe used at above-mentioned in situ hybridization selection and a MARATHON™ cDNA Amplification Kit (CLONTECH). Genetic information from the DNA database of Japan (DDBJ) was utilized in part to isolate FILIP cDNA. Consequently, two full-length FILIP cDNAs, different only in their 5'termini, with regions recognizing the aforementioned probes were obtained. Amino acid sequences were determined from the information of the two cDNA information respectively. The structure is shown in FIG. 1b. As a result, structures were confirmed to coincide with each other except S-FILIP (short form FILIP; GENBANK™ accession number D87257) lacked 247 residues at N-terminus of L-FILIP (long form FILIP; GENBANK™ accession number AB055759). The above-mentioned two proteins were confirmed to be intracellular proteins, since neither a signal sequence nor a transmembrane region was found by their hydrophobicity profiles. Though four leucine zipper motifs and coiled-coil region could be recognized in the C-terminal halves of S-FILIP (FIG. 1c), the amino acid sequence of the regions were found that they did not show similarity to any protein which had been reported so far (FIGS. 1b, c).

Next, in order to investigate the cellular localization of S-FILIP (fiber-like; FIG. 1d top) and L-FILIP (punctate; FIG. 1d bottom), mammalian expression vectors including FILIPs-GFP (pEGFP-N1 (CLONTECH), pCAGGS (Invitrogen) or pBudCE4 (Invitrogen)) which was tagged with green fluorescent protein (GFP) at C-termini of FILIP were transfected to COS-7 cells which were maintained in Dulbecco's modified Eagle medium (DMEM) containing 10% fetal bovine serum (FBS) at 37° C. in 5% $CO_2$, FILIPs-GFP was expressed, and image analysis was performed by OLYMPUS™ IX-70 micro scope equipped with a digital cooled CCD camera (Hamamatsu Photonics) (GFP in FIG. 1d). Further, in order to investigate whether above-mentioned FILIPs were coexistent with F-actin, after aforementioned COS-7 cells were fixed with 4% paraformaldehyde/0.1 M phosphate buffer (PB) (pH 7.4) for 10 min, and permeabilized in 0.1% TRITON® X-100/phosphate buffered saline (PBS) for 3 min, F-actin was stained with rhodamine-phalloidin (1:40; Molecular Probes) (phalloidin in FIG. 1d), coexistence of S-FILIP or L-FILIP with F-actin was investigated (merged in FIG. 1d). The results are shown in FIG. 1d. The scale bar in FIG. 1d indicates 10 µm. According to this result, S-FILIP tagged with GFP was localized along actin stress filaments generally except at their ends, and that the possibility of colocalization of S-FILIP with F-actin was presumed. In contrast, L-FILIP exhibited a punctate distribution in cytoplasm, unlike the colocalization of F-actin.

Meanwhile, 50 cells expressing S-FILIP tagged with above-mentioned GFP (FIG. 1e) or L-FILIP tagged with above-mentioned GFP (FIG. 1f) were extracted in a random order respectively, and the numbers of cells in each expression distribution pattern of FILIPs-GFP were measured. The measurement was performed four times, and the obtained results were calculated as the mean value±S.E.M. The result showed that each pattern of colocalization was heavily dependent on the type of FILIP molecule. Then, coexistence with F-actin in the region not including known actin-binding domain (N-terminus at S-FILIP) was investigated, as well. Expressions of S-FILIPΔC-GFP (C-terminus-deficient S-FILIP tagged with GFP), FILIPΔN (N-terminus-deficient FILIP tagged with GFP), or only GFP at COS-7 cell in the above-mentioned manner (FIG. 1g) suggested that S-FILIP coexist with F-actin (FIG. 1 center) despite the lack of existence of known actin-binding domain. This led to reveal that C-terminal halves (FILIPΔN) being common to S-FILIP and L-FILIP was essential and sufficient for colocalization with F-actin. In contrast, L-FILIP showed little colocalization with F-actin, however, it exhibited a punctate distribution in cytoplasm of the most cells. Further, actin stress filaments were scarcely observed in COS-7 cells which express L-FILIP. The scale bar in FIG. 1g indicates 20 µm.

Example 2

Interaction of FILIPs with Actin Binding Protein Filamin 1

In order to further examine the unique localization of S-FILIP associated with F-actin, and elucidate the factor that might serve as a link between both molecules, a yeast two-hybrid screen was performed using the C-terminal half of S-FILIP (bait) and the whole embryo library (prey) of mouse E11. Using MATCHMAKER™ Two-Hybrid system (CLONTECH) for a yeast two-hybrid screen, the whole embryo library derived from brain of E11 mouse preintegrated into MATCHMAKER™ library (CLONTECH) was transformed with yeast strain PJ69-2A which was transformed with pAS2-1 plasmid vector carrying cDNA that encoded the common C-terminal region of FILIPs (residues 508-965 of the deduced amino acid sequence of S-FILIP), and C-terminal half of S-FILIP were mated with the whole embryo library of E11 mouse. As a result, over $8 \times 10^6$ clones were screened and 17 clones were selected based on three selection markers. In that way, a clone encoding Filamin 1, a protein interacting with actin filament, that interacts with F-actin into isotropic, orthogonal arrays and increases the viscosity and stiffness of the F-actin network was identified from these clones.

Figure 2:
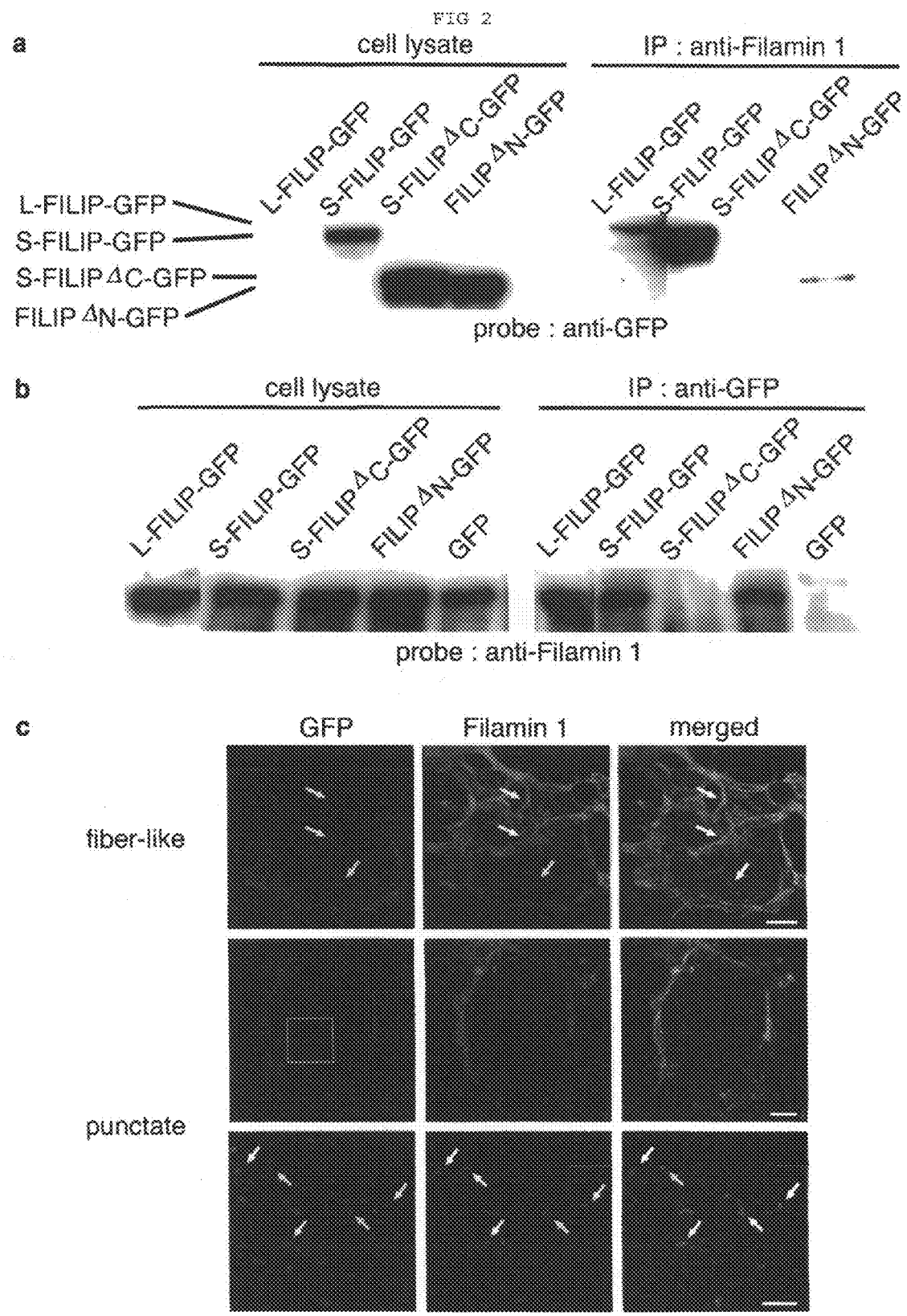
FIG. 2 is a photograph showing the results as to the interaction of L-FILIP or S-FILIP of the present invention with Filamin 1 that is an actin-binding protein.

Next, L-FILIP-GFP, S-FILIP-GFP, a fusion protein where GFP bound to N-terminal half of S-FILIP tagged with GFP (S-FILIPΔC-GFP), a fusion protein where GFP bound to C-terminal half common to FILIPs (FILIPΔN-GFP), or cell lysates obtained from COS-7 cells expressing only GFP (protein solution solubilized in a buffer containing 20 mM TRIS™, (pH 7.5), 150 mM NaCl, 1000 U/ml DNase I, 1% NP-40, 1 mM phenylmethanesulfonyl fluoride, 5 µg/ml aprotinin, 1.5 µM pepstatin A, 2 µM leupeptin) were immunoprecipitated using either anti-GFP antibodies (CLONTECH) or anti-filamin 1 antibodies (Chemicon), and immunoprecipitated protein was detected with anti-Filamin 1 or anti-GFP antibodies as probes. The results of immunoprecipitation with anti-GFP antibodies are shown in FIG. 2a, and the results of immunoprecipitation with anti-Filamin 1 antibodies are shown in FIG. 2b. These results led to confirm the formation of complex comprising either full-length FILIPs or S-FILIP having C-terminal half and Filamin 1.

Further, in order to perform immunocytochemistry, or examine colocalization of S-FILIP (fiber-like; FIG. 2c) or L-FILIP (punctate; FIG. 2c) with Filamin 1, S-FILIP-GFP or L-FILIP-GFP was transfected with COS-7 cell, the cells were fixed to be permeabilized, and image analysis was performed with an OLYMPUS™ IX-70 microscope equipped with a digital cooled CCD camera (Hamamatsu Photonics) in following manner as mentioned in Example 1. After abovementioned cells were permeabilized, the expression of endogenous Filamin 1 was blocked in 10% goat serum/PBS for 20 min, incubated in the coexistence of anti-Filamin 1 antibodies (1:200; Chemicon), then incubated and stained in the coexistence of anti-mouse Ig-Cy3 (1:400; Amersham-Pharmacia). These results are shown in FIG. 2c. Arrows in the figure indicate signals of FILIPs-GFP and Filamin 1 colocalizing interactively. The scale bars in upper and middle columns of the figure indicate 10 μm, and the scale bar in the lower column of the figure indicates 3 μm. As a result, it was confirmed that although not all but most of Filamin 1 were coexisted with S-FILIP signals (FIG. 2c). In cells expressing L-FILIP, about half of the punctate signals were confirmed to colocalized with Filamin 1 punctate signals. Accordingly, the present inventors designated these novel molecules Filamin 1-interacting proteins, FILIPs.

Example 3

Degradation of Filamin 1 by FILIPs and Decrease of Cell Motility by the Degradation Since Filamin 1 is deeply involved in cell migration in various cells (Science 255, 325-327, 1992), it is probable that FILIPs control cell migration via Filamin 1. Thus, investigation was performed whether or not FILIPs affect cell migration rate by introducing FILIPs into COS-7 cells, which possessed Filamin 1 but not FILIPs. On the day after plating (approximately $1 \times 10^4$ cells per 1.88 cm$^2$ area), for analyzing the ratio of cell migration rate, COS-7 cells were transfected with expression vectors including S-FILIP-GFP (FIG. 3a left), L-FILIP-GFP (FIG. 3a center), and GFP only (FIG. 3a right). After 36 to 48 h of transfection, the cells were cultured in Dulbecco's modified Eagle medium (DMEM) containing 10% fetal bovine serum (FBS) on an IX-70 microscope equipped with n IX-IBC culturing apparatus (OLYMPUS™) under low cell density condition, image was analyzed twice at an interval of 120 min (FIG. 3a). [The images of GFP in FIG. 3a (green) were analyzed at an interval of 120 min, and then after the later ones had been converted to red color, these two images were merged.]. Further, in order to quantify cell migration in FIG. 3a, migrating distance (the mean value±s.e.m.) of each of the nucleus (n=20 for S-FILIP-GFP, n=19 for L-FILIP-GFP, and n=18 for GFP alone) was measured by each group at an interval of 120 min (FIG. 3b). The scale bar in FIG. 3a shows 50 μm, in FIG. 3b, the cell migration occurred in the second image analysis was quantified by using phase-contrast image in combination. According to these results, it was confirmed that cell migration rate of the cells expressing FILIPs-GFP was reduced compared with the cells expressing GFP alone, under low cell density conditions, in which cell can migrate freely without interfering with other cells as well.

Next, in order to elucidate the effect of FILIPs on lamellipodium formation, a wound healing assay was performed. Over-confluent COS-7 cells were transfected with the expression vectors including either FILIPs-GFP or GFP. After 36 to 48 h of transfention, defects were made among cells (FIG. 3b), and after they were cultured for further 3 h, they were fixed and stained with rhodamine-phalloidn. After the staining, the defect edges among the cells were observed to confirm whether they had lamellipodia. The results are shown in FIG. 3c. Arrows in the figure show the defect edges at the S- and L-FILIP-GFP expression cells, arrowheads show the neighboring cells that express no FILIPs respectively, the scale bar indicates 50 μm. Among the aforementioned COS-7 cells which formed defects, 50 cells were extracted at random, the cells where lamellipodium were formed at the wound edge and green GFP signals (FILIPs-GFP or GFP alone) were seen in the region were counted among them. As a result, it was confirmed that most of quiescent cells in the over-confluent state developed lamellipodia (sheet-like processes) in response to migration of neighboring cells. As shown in FIG. 3c, most cells expressing S- or L-FILIP-GFP did not form lamellipodia at the wound edge, compared with the cells that did not express FILIPs. In the cells expressing GFP (control), formation rate of lamellipodia was 68% at their wound edges, whereas formation rate of lamellipodia in the cells expressing S- and L-FILIP-GFP were only 28% and 4%, respectively. These results suggest that FILIPs suppress lamellipodium formation and cell migration, and lead to the consideration that FILIPs has inhibitory effects for the function of Filamin 1.

The molecular mechanism for the inhibitory effects of FILIPs on Filamin 1 was further examined by expressing recombinant FILIPs and recombinant Filamin 1 simultaneously in the same COS-7 cells using single expression vector including dual promoters. As shown in FIG. 3d, IRES (internal ribosomal entry site) sequence was inserted between HA-tagged Filamin 1 cDNA (HA-Filamin 1) and GFP cDNA, Filamin 1 and GFP were transcribed with CMV promoter (p), and FILIPs were integrated into expression vector for mammal cell (pBudCE4; Invitrogen) so as to be transcribed and expressed with EF-1α promoter (p'), and transfected into COS-7 cells. Then, they were cultured in the presence or absence of 50 μm calpeptine in addition to the conditions of example 1, and expression amount of HA-Filamin 1 and GFP were confirmed by SDS-PAGE method. Further, HA-Filamin 1 and GFP were confirmed that they were translated from the same mRNA in the cell. The relative amount of HA-Filamin 1 that expressed at COS-7 cells in the presence or absence of S-FILIP (S) or L-FILIP (L) was measured on the basis of GFP expression amount. (The relative amount of recombinant Filamin 1 and GFP was 4.7 in the absence of FILIPs and 1.8 in the presence of S-FILIP.) These results are shown in FIG. 3d. This revealed that the expression amount of Filamin 1 was decreased in the presence of FILIPs, especially of L-FILIP. It shows little HA-Filamin 1 protein exists in the presence of mRNA of HA-Filamin 1 and GFP. However, it was suggested that FILIPs induced degradation of Filamin 1, since these effects were lost in the presence of calpeptine which is a protease inhibitor.

Meanwhile, COS-7 cells expressing L-FILIP-GFP were generated in the same manner as mentioned in example 2, and immunoreactivity of them against Filamin 1 was examined. The results are shown in FIG. 3e. Arrows in the figure indicate COS-7 cells expressing L-FILIP-GFP, the scale bar in the figure indicates 25 μm. As a result, at COS-7 cells expressing L-FILIP-GFP, especially the amount of endogenous Filamin 1 was remarkably declined compared with adjacent cells which do not express FILIP. It led to that COS-7 cells expressing L-FILIP-GFP showed law immunoreactivity against Filamin 1. It was also revealed that L-FILIP showed higher activity compared with S-FILIP in degradation of Filamin 1. That is, because S-FILIP does not degrade Filamin 1 abundantly, although most of S-FILIPs in cells colocalize with Filamin 1 and F-actin, the punctate distribution of F-actin, which was observed in COS-7 cells expressing L-FILIP, was also observed even in a small fraction of cells expressing S-FILIP. Moreover, induction of degradation of Filamin 1 protein associated with FILIPs can be thought as one of causes which brings low immunoreactivity against Filamin 1 colocalizing with FILIPs (particularly L-FILIP) as shown in FIG. 2c.

Example 4

Figure 4:
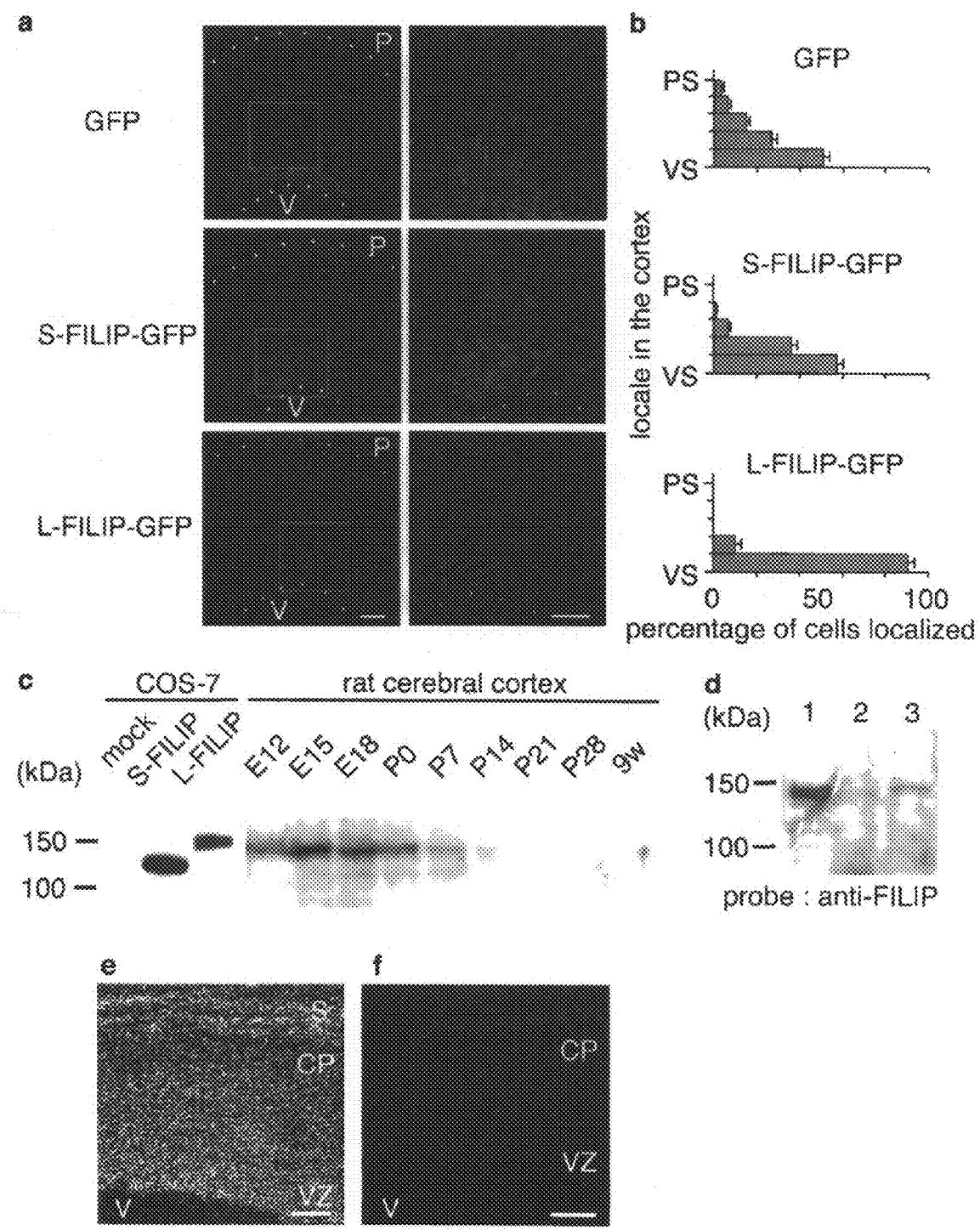
FIG. 4 is a photograph showing the results as to control of cell migration from ventricular zone by L-FILIP or S-FILIP in the formation of neocortex.

Regulation of Cell Migration from Ventricular Zone by FILIPs in Developing Neocortex Since FILIPs introduced into COS-7 cells exert inhibitory effects on cell migration as well as inducing degradation of Filamin 1, when Filamin 1 gene is mutated, postmitotic cells affected by the mutation remain in the ventricular zone, and cause malformation of human cortical. It is likely that FILIPs play a pivotal role in the control of cell migration in the developing neocortex (Neuron 16, 77-87, 1996, Neuron 21, 1315-1325, 1998). Thus, in order to examine the role of FILIPs on neuronal migration in vivo, plasmid DNA (S-FIL-IPS-GFP cDNA, L-FILIPS-GFP cDNA, or GFP cDNA) was administered into the lateral ventricle of E18 rat brain, then plasmid DNA were incorporated to ventricular zone cells by delivering electrical pulses with a square-pulse electroporator (BEX). The brain of E18 rat was sliced coronally into 200 μm with a microtome, and the dorsal portion of the cortex was dissected out and cultured for four days on a collagen-coated membrane (TRANSWELL®-COL, COSTAR®-Corning) in a DMEM/F12 medium containing 10% FBS and N2 supplement. After cultured, the obtained cortex sections were fixed with 4% paraformaldehyde/0.1 M PB (pH 7.4) and their images were analyzed on a ZEISS™ LSM510 laser-scanning confocal microscope (ZEISS™) (FIG. 4a). In FIG. 4a, each of the drawings in the right shows enlarged illustration of inside of the frames in each of the drawings in the left. White dots, p, and V show the edges of the section, pial surface, and lateral ventricle, respectively. Scale bars in FIG. 4a indicate 200 μm (left) and 100 μm (right). The migration rate of each cell against GFP or FILIPs-GFP was obtained by determining the quantity of cells at each site of cortex [cortex was divided equally into five section from lateral ventricle side (VS) to pial surface side (PS)] which were on the fourth day since they were cultured (FIG. 4b). The value of S-FILIP-GFP was obtained from three sections, while that of L-FILIP-GFP was obtained from five sections and the mean value were calculated as ±s.e.m., respectively.

Consequently, in GFP-expressing cells (GFP) as control, it was confirmed that a number of labeling cells localizing in the ventricular zone was migrating out towards pial surface. These cells were spindle-shaped with leading and trailing processes oriented cortex radially (Neurosci. Res. (Suppl.) 24, S18, 2000). In contrast, cells expressing S— or L-FILIP-GFP were quite different in shape and migration rate from those of GFP-expressing cells only. These expressing cells were round, did not spread long and radially, and hardly migrated staying around neighborhood of the ventricular zone. These effects of FILIPs in ventricular zone cells were consistent with those in COS-7 cells. Fewer cells expressed L-FILIP-GFP compared with GFP or S-FILIP-GFP. The number of cells expressing L-FILIP-GFP did not show significant difference even where they were cultured. These might be caused by the low efficiency of the transfection or translation.

Next, the ontogenetic expression profiles of L- and S-FIL-IPs in developing rat neocortex were analyzed by immunoblotting with anti-FILIP antibodies. The results are shown in FIG. 4c. The above-mentioned anti-FILIP antibodies (polyclonal anti-FILIP antibody) were prepared with rabbits immunized by synthesized peptide equivalent to the $892^{nd}$ to $909^{th}$ residues of the amino acid sequence of S-FILIP, as the method described in J. Neurochem. 75, 1-8, 2000. From this result, L-FILIP was confirmed more remarkably than S-FILIP in cortex developing process. S-FILIP and L-FILIP appear to play similar roles, however, it is apparent that L-FILIP is the major partner of Filamin 1 in the developing neocortex, since L-FILIP expresses at higher level and shows higher capacity for inducing Filamin 1 degradation. Expression of filips mRNA was low on E18, it is likely that already transcribed FILIP proteins remain in sufficient amounts.

Because filips express in ventricular zone, it is likely that FILIPs interact with Filamin 1 gene and induce the degradation in ventricular zone. Cortical solution of E12 rat [protein solution solubilized with a buffer containing 20 mM TRIS™ (pH 7.5), 150 mM NaCl, 1000 U/ml DNase I, 1% NP-40, 1 mM phenylmethanesulfonyl fluoride, 5 μg/ml aprotinin, 1.5 μM pepstatin A, 2 μM leupeptin] were immunoprecipitated using either anti-Filamin 1 antibodies or anti-c-Myc antibodies (Santa Cruz), and protein was detected using anti-FILIP antibody as a probe. The results are shown in FIG. 4d. The results show that L-FILIP was detected from neocortex solution of E12 rat, while S-FILIP was hardly detected (line 1 in FIG. 4d). Further, since L-FILIP was coimmunoprecipitated with anti-Filamin 1 antibodies in the same solution (line 3 in FIG. 4d), it was revealed that endogenous FILIP (L-FILIP mainly) interacted with endogenous Filamin 1. However, anti-c-Myc antibodies (control) did not show any positive signal (line 2 in FIG. 4d).

It has been known that Filamin 1 protein expresses in migrating and postmigratory neurons in the intermediate zone and the cortical plate of human embryonic brain (Neuron 21, 1315-1325, 1998). Expression of Filamin 1 at rat cerebral cortex was examined with in situ hybridization histochemical study. The results are shown in FIG. 4e. In the figure, CP, S, V, and VZ indicates cortical plate, cranium, lateral ventricle, and ventricular zone, respectively. The scale bar shows 100 μm. The expression of Filamin 1 gene could be confirmed all through the developing cortex, particularly the high expression in ventricular zone was confirmed from these results. Further, expression of the above-mentioned Filamin 1 at cerebral cortex of rat was examined with immunohistochemistry. Frozen sections prepared from E16 rat cerebral cortices fixed with the Zamboni's solution [0.1 M PB (pH 7.4), 2% paraformaldehyde, 0.21% picric acid] were air-dried, permeabilized with PBS containing 0.2% TRITON® X-100, 0.5% bovine serum albumin for 30 min and incubated in the coexistence of anti-Filamin antibodies (1:40; Sigma), followed by incubation in the coexistence of anti-goat IgG antibodies bound with fluorescein (1:100; Jackson ImmunoResearch Laboratories) and stained. The results are shown in FIG. 4f. In the figure, CP, V, and VZ indicate cortical plate, lateral ventricle, and ventricular zone, respectively. The scale bar shows 100 μm. It was revealed by these results that ventricular zone cell highly expressed Filamin 1 gene, while Filamin-like immunoreactivity was lower than those observed in the intermediate zone and cortical plate. Since Filamin 1 is closely related to cell migration (Science 255, 325-7, 1992, Neuron 21, 1315-25, 1998), it is likely that degradation of Filamin 1 in the ventricular zone through the action of FILIPs is a significant process for controlling the start of migration. The process is a unique molecular mechanism of inhibitory control over radial migration of cells out of the ventricular zone during developing cortex.

INDUSTRIAL APPLICABILITY

The proteins having effects of controlling cell migration and cell death and DNA encoding the proteins are control molecules of cytoskeletal protein. Therefore, they are applicable for an inhibitor for metastasis of a cancer or a tumor or a regulant of cell migration for transplantation treatment as well as for controlling cell motility and cell death. They are further applicable for controlling cell motility and cell death, screening for promoters or inhibitors of effects of controlling cell migration and/or cell death, and promoters or inhibitors for expressing the proteins/peptides of the present invention, and etc. by using the aforementioned proteins having effects of controlling cell motility and cell death and DNA encoding the proteins. Furthermore, using the proteins/peptides of the present invention makes it possible to reveal the mechanisms of metastasis of a cancer or a tumor, cell migration of neuron and the like.

The invention claimed is:

1. An isolated protein comprising an amino acid sequence selected from the group consisting of SEQ ID NO:2, SEQ ID NO:4 and SEQ ID NO:6, wherein the said protein degrades Filamin 1 to control cell migration and cell death.

2. The isolated protein of claim 1, wherein said protein is encoded by a DNA selected from the group consisting of SEQ ID NO: 1, SEQ ID NO:3 and SEQ ID NO:5.

3. A fusion protein comprising the isolated protein of claim 1 bound to a marker protein.

* * * * *

SEQUENCE LISTING

```
<160> NUMBER OF SEQ ID NOS: 6

<210> SEQ ID NO 1
<211> LENGTH: 4364
<212> TYPE: DNA
<213> ORGANISM: Rattus norvegicus
<220> FEATURE:
<221> NAME/KEY: CDS
<222> LOCATION: (75)..(3710)

<400> SEQUENCE: 1
ccactgggtt cttcaaggga taaaccagcg gcgaaagaac acaccattgg ttaaggagtc        60
gacaacaggt ggga atg aga tca cga aat caa ggt gga gaa agt tca tct        110
             Met Arg Ser Arg Asn Gln Gly Gly Glu Ser Ser Ser
              1               5                   10 aac ggg cat gtc tcc tgc ccc aag tcc tcc atc atc agc agt gat ggt        158
Asn Gly His Val Ser Cys Pro Lys Ser Ser Ile Ile Ser Ser Asp Gly
             15                  20                  25 ggt aag ggc ccc tca gaa gat gca aaa aag aac aag gcc aat cgg aag        206
Gly Lys Gly Pro Ser Glu Asp Ala Lys Lys Asn Lys Ala Asn Arg Lys
         30                  35                  40 gag gag gat gtc atg gct tcc gga act atc aaa agg cac ctc aaa cca        254
Glu Glu Asp Val Met Ala Ser Gly Thr Ile Lys Arg His Leu Lys Pro
     45                  50                  55                  60 tct gga gaa agt gag aaa aag act aag aag tct gtg gag tta tcc aag        302
Ser Gly Glu Ser Glu Lys Lys Thr Lys Lys Ser Val Glu Leu Ser Lys
                 65                  70                  75 gag gac ctc atc cag ctc ctg agt atc atg gaa ggg gag ttg cag gct        350
Glu Asp Leu Ile Gln Leu Leu Ser Ile Met Glu Gly Glu Leu Gln Ala
             80                  85                  90 cga gaa gat gtc atc cac atg ctg agg aca gag aaa acc aag ccc gag        398
Arg Glu Asp Val Ile His Met Leu Arg Thr Glu Lys Thr Lys Pro Glu
         95                 100                 105 gtt ctg gag gca cac tat gga tct gca gaa cct gag aaa gtg ctt cgg        446
Val Leu Glu Ala His Tyr Gly Ser Ala Glu Pro Glu Lys Val Leu Arg
    110                 115                 120 gtc ctg cac cga gat gcc atc ctt gct caa gag aag tcc ata gga gaa        494
Val Leu His Arg Asp Ala Ile Leu Ala Gln Glu Lys Ser Ile Gly Glu
125                 130                 135                 140 gac gtc tat gag aaa cct atc tca gag ctg gac aga ctg gag gaa aag        542
Asp Val Tyr Glu Lys Pro Ile Ser Glu Leu Asp Arg Leu Glu Glu Lys
                145                 150                 155 cag aag gag acg tac cgc cgc atg cta gag cag ctg ctg ctg gct gag        590
Gln Lys Glu Thr Tyr Arg Arg Met Leu Glu Gln Leu Leu Leu Ala Glu
            160                 165                 170 aag tgt cac agg cgc acc gtg tac gag ctg gag aac gag aag cac aag        638
Lys Cys His Arg Arg Thr Val Tyr Glu Leu Glu Asn Glu Lys His Lys
        175                 180                 185
```

```
                                            -continued
cac act gac tac atg aac aag agc gac gac ttc acc aac ctg ctg gag        686
His Thr Asp Tyr Met Asn Lys Ser Asp Asp Phe Thr Asn Leu Leu Glu
    190                 195                 200 cag gag cga gag agg ttg aaa aag ctc ctt gaa caa gaa aaa gct tac        734
Gln Glu Arg Glu Arg Leu Lys Lys Leu Leu Glu Gln Glu Lys Ala Tyr
205                 210                 215                 220 caa gcc cgc aaa gaa aag gaa aac gct aag cgg ctc aac aaa ctt cga        782
Gln Ala Arg Lys Glu Lys Glu Asn Ala Lys Arg Leu Asn Lys Leu Arg
                225                 230                 235 gat gag ctt gtg aag ctc aag tcc ttc gcc ctc atg ttg gtg gac gag        830
Asp Glu Leu Val Lys Leu Lys Ser Phe Ala Leu Met Leu Val Asp Glu
                    240                 245                 250 agg cag atg cac atc gag caa ctg ggc ctg cag agt cag aaa gtc cag        878
Arg Gln Met His Ile Glu Gln Leu Gly Leu Gln Ser Gln Lys Val Gln
                255                 260                 265 gac ctc act cag aag ctg agg gag gag gaa gaa aaa ctc aaa gcg gtc        926
Asp Leu Thr Gln Lys Leu Arg Glu Glu Glu Glu Lys Leu Lys Ala Val
270                 275                 280 act tac aaa tcc aag gaa gac cgc cag aag ctg ctc aag tta gaa gtg        974
Thr Tyr Lys Ser Lys Glu Asp Arg Gln Lys Leu Leu Lys Leu Glu Val
285                 290                 295                 300 gac ttc gaa cac aag gcc tcg agg ttt tcc cag gag cac gaa gag atg       1022
Asp Phe Glu His Lys Ala Ser Arg Phe Ser Gln Glu His Glu Glu Met
                305                 310                 315 aac gcc aaa ttg gcg aat caa gaa tct cac aac cgg caa ctt cga ctc       1070
Asn Ala Lys Leu Ala Asn Gln Glu Ser His Asn Arg Gln Leu Arg Leu
                320                 325                 330 aaa ctg gtt ggc tta tcg caa agg att gag gag ctg gaa gag acc aat       1118
Lys Leu Val Gly Leu Ser Gln Arg Ile Glu Glu Leu Glu Glu Thr Asn
                    335                 340                 345 aaa agc ctt cag aag gca gag gaa gag ctc cag gag ctg aga gag aaa       1166
Lys Ser Leu Gln Lys Ala Glu Glu Glu Leu Gln Glu Leu Arg Glu Lys
                350                 355                 360 att gcc aaa ggg gaa tgt gga aac tcc agt ctc atg gcg gaa gtg gag       1214
Ile Ala Lys Gly Glu Cys Gly Asn Ser Ser Leu Met Ala Glu Val Glu
365                 370                 375                 380 agt ctg cgc aag cgc gtg ctt gag atg gag ggc aag gat gaa gag atc       1262
Ser Leu Arg Lys Arg Val Leu Glu Met Glu Gly Lys Asp Glu Glu Ile
                385                 390                 395 acg aag acc gag gcc cag tgc cgg gag ctg aag aag aag ctc caa gag       1310
Thr Lys Thr Glu Ala Gln Cys Arg Glu Leu Lys Lys Lys Leu Gln Glu
                400                 405                 410 gaa gaa cac cac agc aag gaa ctt aga cta gaa gtg gag aag ctg cag       1358
Glu Glu His His Ser Lys Glu Leu Arg Leu Glu Val Glu Lys Leu Gln
                415                 420                 425 aag agg atg tct gag ctg gag aag ctg gag gaa gcg ttc agc cgg agt       1406
Lys Arg Met Ser Glu Leu Glu Lys Leu Glu Glu Ala Phe Ser Arg Ser
        430                 435                 440 aag tcg gaa tgc acc cag ctc cat ctg aac ctg gag aag gag aag aac       1454
Lys Ser Glu Cys Thr Gln Leu His Leu Asn Leu Glu Lys Glu Lys Asn
445                 450                 455                 460 cta acc aaa gac ctg ctg aac gag ctg gag gtg gtc aag agt cga gtt       1502
Leu Thr Lys Asp Leu Leu Asn Glu Leu Glu Val Val Lys Ser Arg Val
                    465                 470                 475 aaa gaa ctc gaa tgc tcc gag agt aga ctg gag aag gcc gag tta agc       1550
Lys Glu Leu Glu Cys Ser Glu Ser Arg Leu Glu Lys Ala Glu Leu Ser
                480                 485                 490 ctc aaa gat gac ctt aca aag ctg aag tcc ttc act gtg atg ctg gtg       1598
Leu Lys Asp Asp Leu Thr Lys Leu Lys Ser Phe Thr Val Met Leu Val
                495                 500                 505
```

-continued

```
gat gag agg aaa aat atg atg gag aaa ata aag caa gaa gag agg aaa      1646
Asp Glu Arg Lys Asn Met Met Glu Lys Ile Lys Gln Glu Glu Arg Lys
    510                 515                 520 gtg gat ggg ttg aat aaa aac ttt aag gtg gag cag gga aaa gtc atg      1694
Val Asp Gly Leu Asn Lys Asn Phe Lys Val Glu Gln Gly Lys Val Met
525                 530                 535                 540 gat gtg acg gaa aag cta atc gag gaa agc aag aag ctt tta aaa ctc      1742
Asp Val Thr Glu Lys Leu Ile Glu Glu Ser Lys Lys Leu Leu Lys Leu
                545                 550                 555 aaa tct gaa atg gag gaa aag gag tac agt ctg aca aag gag agg gat      1790
Lys Ser Glu Met Glu Glu Lys Glu Tyr Ser Leu Thr Lys Glu Arg Asp
                    560                 565                 570 gag ctg atg ggt aaa ctg agg agc gaa gaa gaa agg tcc tgt gaa ctg      1838
Glu Leu Met Gly Lys Leu Arg Ser Glu Glu Glu Arg Ser Cys Glu Leu
                575                 580                 585 agc tgc agt gta gac tta cta aag aag cgg ctt gat ggc ata gag gag      1886
Ser Cys Ser Val Asp Leu Leu Lys Lys Arg Leu Asp Gly Ile Glu Glu
            590                 595                 600 gta gaa agg gaa ata aac cga ggt agg tcg tgc aag ggg tct gag ttc      1934
Val Glu Arg Glu Ile Asn Arg Gly Arg Ser Cys Lys Gly Ser Glu Phe
605                 610                 615                 620 acc tgc ccg gaa gac aat aag atc aga gaa cta acg ctt gaa atc gag      1982
Thr Cys Pro Glu Asp Asn Lys Ile Arg Glu Leu Thr Leu Glu Ile Glu
                625                 630                 635 aga ctg aag aaa cgg ctc cag cag ttg gag gtg gtg gag ggg gac ttg      2030
Arg Leu Lys Lys Arg Leu Gln Gln Leu Glu Val Val Glu Gly Asp Leu
                    640                 645                 650 atg aag acc gag gac gaa tat gac cag ttg gag cag aag ttc aga acc      2078
Met Lys Thr Glu Asp Glu Tyr Asp Gln Leu Glu Gln Lys Phe Arg Thr
                655                 660                 665 gag cag gat aag gca aac ttc ctc tcc cag cag ctc gag gaa atc aaa      2126
Glu Gln Asp Lys Ala Asn Phe Leu Ser Gln Gln Leu Glu Glu Ile Lys
            670                 675                 680 cac caa atg gcc aag cac aaa gcc ata gag aaa ggg gag gcc gtg agc      2174
His Gln Met Ala Lys His Lys Ala Ile Glu Lys Gly Glu Ala Val Ser
685                 690                 695                 700 cag gaa gcc gaa ctg cga cac agg ttt cgg ctg gag gag gct aaa agt      2222
Gln Glu Ala Glu Leu Arg His Arg Phe Arg Leu Glu Glu Ala Lys Ser
                705                 710                 715 cgt gat tta cag gcc gag gtg cag gct ctc aag gag aag atc cac gag      2270
Arg Asp Leu Gln Ala Glu Val Gln Ala Leu Lys Glu Lys Ile His Glu
                    720                 725                 730 ctg atg aac aag gaa gac cag ctg tct cag ctc caa gtc gac tat tcg      2318
Leu Met Asn Lys Glu Asp Gln Leu Ser Gln Leu Gln Val Asp Tyr Ser
                735                 740                 745 gtc ctt cag caa aga ttt atg gaa gaa gaa act aag aac aag aac atg      2366
Val Leu Gln Gln Arg Phe Met Glu Glu Glu Thr Lys Asn Lys Asn Met
            750                 755                 760 ggg agg gag gtc ctc aat ctg acc aag gag cta gag ctt tcc aag cgc      2414
Gly Arg Glu Val Leu Asn Leu Thr Lys Glu Leu Glu Leu Ser Lys Arg
765                 770                 775                 780 tac agc cga gct ctc agg ccg agt ggg aac ggc cga agg atg gtg gac      2462
Tyr Ser Arg Ala Leu Arg Pro Ser Gly Asn Gly Arg Arg Met Val Asp
                785                 790                 795 gtg cct gtg gcc tcc act ggg gtg cag acc gag gcg gtg tgc ggg gat      2510
Val Pro Val Ala Ser Thr Gly Val Gln Thr Glu Ala Val Cys Gly Asp
                    800                 805                 810 gct gcg gag gag gag acc ccg gct gtg ttc att cgc aaa tcc ttc cag      2558
Ala Ala Glu Glu Glu Thr Pro Ala Val Phe Ile Arg Lys Ser Phe Gln
```

-continued

|  |  |  |  |  |  |  |  |  |  |  |  |  |  |  |  |
|---|---|---|---|---|---|---|---|---|---|---|---|---|---|---|---|
|  |  | 815 |  |  |  | 820 |  |  |  | 825 |  |  |  |  |  |

```
                                 815                 820                 825
gag gaa aat cac atc atg agt aat ctt cga cag gta ggc ctg aag aaa                2606
Glu Glu Asn His Ile Met Ser Asn Leu Arg Gln Val Gly Leu Lys Lys
        830                 835                 840 ccc atg gaa cgg tcc tcg gtc ctc gac agg tat ccc cca gca gcg aat                2654
Pro Met Glu Arg Ser Ser Val Leu Asp Arg Tyr Pro Pro Ala Ala Asn
845                 850                 855                 860 gag ctc acc atg agg aag tct tgg att cct tgg atg aga aaa aga gaa                2702
Glu Leu Thr Met Arg Lys Ser Trp Ile Pro Trp Met Arg Lys Arg Glu
                865                 870                 875 aac ggt cct tcc act ccg cag gag aaa ggg ccc agg cca aac cag ggt                2750
Asn Gly Pro Ser Thr Pro Gln Glu Lys Gly Pro Arg Pro Asn Gln Gly
        880                 885                 890 gca ggg cac ccc ggg gag ctg gtc cta gca cca aag cag ggc cag ccc                2798
Ala Gly His Pro Gly Glu Leu Val Leu Ala Pro Lys Gln Gly Gln Pro
    895                 900                 905 cta cac atc cgt gtg aca cca gat cat gag aac agc act gcc acc ctg                2846
Leu His Ile Arg Val Thr Pro Asp His Glu Asn Ser Thr Ala Thr Leu
910                 915                 920 gag atc aca agc ccc aca tct gaa gag ttt ttc tct agt acc acc gtc                2894
Glu Ile Thr Ser Pro Thr Ser Glu Glu Phe Phe Ser Ser Thr Thr Val
925                 930                 935                 940 att cct acc tta ggc aac cag aaa cca aga ata acc att att cca tca                2942
Ile Pro Thr Leu Gly Asn Gln Lys Pro Arg Ile Thr Ile Ile Pro Ser
            945                 950                 955 ccc aat gtc atg tcg caa aag ccc aaa agt gca gat cct act ctc ggc                2990
Pro Asn Val Met Ser Gln Lys Pro Lys Ser Ala Asp Pro Thr Leu Gly
        960                 965                 970 cca gaa cga gcc atg tcc cct gtc acg att act act att tcc aga gag                3038
Pro Glu Arg Ala Met Ser Pro Val Thr Ile Thr Thr Ile Ser Arg Glu
    975                 980                 985 aag agc ccg gaa ggt gga agg agc gcc ttt gcc gac agg cct gca tcc                3086
Lys Ser Pro Glu Gly Gly Arg Ser Ala Phe Ala Asp Arg Pro Ala Ser
990                 995                 1000 ccc atc caa atc atg acg gtg tca aca tct gca gct ccc act gaa atc                3134
Pro Ile Gln Ile Met Thr Val Ser Thr Ser Ala Ala Pro Thr Glu Ile
1005                1010                1015                1020 gct gtc tct cct gaa tct cag gaa gtg cct atg gga agg act atc ctc                3182
Ala Val Ser Pro Glu Ser Gln Glu Val Pro Met Gly Arg Thr Ile Leu
            1025                1030                1035 aaa gtc acc ccg gaa aaa caa act gtt cca gcc ccc gtg cgg aag tac                3230
Lys Val Thr Pro Glu Lys Gln Thr Val Pro Ala Pro Val Arg Lys Tyr
        1040                1045                1050 aac tcc aat gct aat atc atc acc acg gaa gac aat aaa att cac att                3278
Asn Ser Asn Ala Asn Ile Ile Thr Thr Glu Asp Asn Lys Ile His Ile
    1055                1060                1065 cac ctg ggt tct cag ttt aag cga tct cct ggg cct gcc gct gaa ggc                3326
His Leu Gly Ser Gln Phe Lys Arg Ser Pro Gly Pro Ala Ala Glu Gly
1070                1075                1080 gtg agc cca gtt atc acc gtc cgg cct gtc aac gtg aca gcg gag aag                3374
Val Ser Pro Val Ile Thr Val Arg Pro Val Asn Val Thr Ala Glu Lys
1085                1090                1095                1100 gag gtt tct aca ggc aca gtc ctt cgc tct ccc agg aac cac ctc tct                3422
Glu Val Ser Thr Gly Thr Val Leu Arg Ser Pro Arg Asn His Leu Ser
            1105                1110                1115 tca aga ccc ggt gct agc aaa gtg acc agc act ata act ata acc ccg                3470
Ser Arg Pro Gly Ala Ser Lys Val Thr Ser Thr Ile Thr Ile Thr Pro
        1120                1125                1130 gtc aca acg tca tcc aca cga gga acc caa tca gtg tca gga caa gat                3518
```

-continued

```
Val Thr Thr Ser Ser Thr Arg Gly Thr Gln Ser Val Ser Gly Gln Asp
            1135                1140                1145 ggg tca tct cag cgg cct acc ccc acc cgc att cct atg tca aaa ggt    3566
Gly Ser Ser Gln Arg Pro Thr Pro Thr Arg Ile Pro Met Ser Lys Gly
    1150                1155                1160 atg aaa gct gga aag cca gta gtg gca gcc tca gga gca gga aat ctg    3614
Met Lys Ala Gly Lys Pro Val Val Ala Ala Ser Gly Ala Gly Asn Leu
1165                1170                1175                1180 acc aaa ttc cag cct cga gct gag act cag tct atg aaa ata gag ctg    3662
Thr Lys Phe Gln Pro Arg Ala Glu Thr Gln Ser Met Lys Ile Glu Leu
                1185                1190                1195 aag aaa tct gca gcc agc agc act gcc tct ctt gga ggg ggg aag ggc    3710
Lys Lys Ser Ala Ala Ser Ser Thr Ala Ser Leu Gly Gly Gly Lys Gly
            1200                1205                1210 tgagggcagt ggctaagggg gtatgttgta aggatgctac tgctgcagtg gaaacaaacc    3770
ttcctctgtg ccaacccttt ccttgtacta ctaatttaag ttttaaatat cttgtttata    3830
aaataaccat ttaatagcca tgcaccccc tcccattttg tgcatctgtt tcaatgcagg    3890
ggaatagaat taattagcag aatttctgtt tgctgaatgt tctgttgaag atgttggtcc    3950
agttcagttt tacttctagc atgtggcccc attcaaggta gctcacgagt tgtgaagccc    4010
tcaatatcgt caccggagag atttgaggac cacattacat atgctcccaa aggctggctc    4070
ccaattttcc taattgtaag ccaactttaa tagactcagt tctgtgattt ttttttccaa    4130
aaaaaaaata ttttgaaata ggacagagtt taacagttgt cattttgcac tatcaagcca    4190
tgagtttgat atatgggtta taagaaaaga atactttcag agctatcaca gggtctctaa    4250
acttttggaa aaacaaaagc ccctaatatg acctcaggaa acaatttgaa catgaaataa    4310
aatggaaatg aactgtggaa tcttaaaaaa aaaaaaaaaa aaaaaaaaaa aaaa          4364
```

<210> SEQ ID NO 2
<211> LENGTH: 1212
<212> TYPE: PRT
<213> ORGANISM: Rattus norvegicus

<400> SEQUENCE: 2

```
Met Arg Ser Arg Asn Gln Gly Gly Glu Ser Ser Ser Asn Gly His Val
1               5                   10                  15

Ser Cys Pro Lys Ser Ser Ile Ile Ser Ser Asp Gly Gly Lys Gly Pro
            20                  25                  30

Ser Glu Asp Ala Lys Lys Asn Lys Ala Asn Arg Lys Glu Glu Asp Val
        35                  40                  45

Met Ala Ser Gly Thr Ile Lys Arg His Leu Lys Pro Ser Gly Glu Ser
    50                  55                  60

Glu Lys Lys Thr Lys Lys Ser Val Glu Leu Ser Lys Glu Asp Leu Ile
65                  70                  75                  80

Gln Leu Leu Ser Ile Met Glu Gly Glu Leu Gln Ala Arg Glu Asp Val
                85                  90                  95

Ile His Met Leu Arg Thr Glu Lys Thr Lys Pro Glu Val Leu Glu Ala
            100                 105                 110

His Tyr Gly Ser Ala Glu Pro Glu Lys Val Leu Arg Val Leu His Arg
        115                 120                 125

Asp Ala Ile Leu Ala Gln Glu Lys Ser Ile Gly Glu Asp Val Tyr Glu
    130                 135                 140

Lys Pro Ile Ser Glu Leu Asp Arg Leu Glu Glu Lys Gln Lys Glu Thr
145                 150                 155                 160
```

-continued

```
Tyr Arg Arg Met Leu Glu Gln Leu Leu Leu Ala Glu Lys Cys His Arg
                165                 170                 175

Arg Thr Val Tyr Glu Leu Glu Asn Glu Lys His Lys His Thr Asp Tyr
            180                 185                 190

Met Asn Lys Ser Asp Asp Phe Thr Asn Leu Leu Glu Gln Glu Arg Glu
        195                 200                 205

Arg Leu Lys Lys Leu Leu Glu Gln Glu Lys Ala Tyr Gln Ala Arg Lys
    210                 215                 220

Glu Lys Glu Asn Ala Lys Arg Leu Asn Lys Leu Arg Asp Glu Leu Val
225                 230                 235                 240

Lys Leu Lys Ser Phe Ala Leu Met Leu Val Asp Glu Arg Gln Met His
                245                 250                 255

Ile Glu Gln Leu Gly Leu Gln Ser Gln Lys Val Gln Asp Leu Thr Gln
            260                 265                 270

Lys Leu Arg Glu Glu Glu Lys Leu Lys Ala Val Thr Tyr Lys Ser
        275                 280                 285

Lys Glu Asp Arg Gln Lys Leu Leu Lys Leu Glu Val Asp Phe Glu His
    290                 295                 300

Lys Ala Ser Arg Phe Ser Gln Glu His Glu Met Asn Ala Lys Leu
305                 310                 315                 320

Ala Asn Gln Glu Ser His Asn Arg Gln Leu Arg Leu Lys Leu Val Gly
                325                 330                 335

Leu Ser Gln Arg Ile Glu Glu Leu Glu Glu Thr Asn Lys Ser Leu Gln
            340                 345                 350

Lys Ala Glu Glu Glu Leu Gln Glu Leu Arg Glu Lys Ile Ala Lys Gly
        355                 360                 365

Glu Cys Gly Asn Ser Ser Leu Met Ala Glu Val Glu Ser Leu Arg Lys
    370                 375                 380

Arg Val Leu Glu Met Glu Gly Lys Asp Glu Glu Ile Thr Lys Thr Glu
385                 390                 395                 400

Ala Gln Cys Arg Glu Leu Lys Lys Lys Leu Gln Glu Glu His His
                405                 410                 415

Ser Lys Glu Leu Arg Leu Glu Val Glu Lys Leu Gln Lys Arg Met Ser
            420                 425                 430

Glu Leu Glu Lys Leu Glu Glu Ala Phe Ser Arg Ser Lys Ser Glu Cys
        435                 440                 445

Thr Gln Leu His Leu Asn Leu Glu Lys Glu Lys Asn Leu Thr Lys Asp
    450                 455                 460

Leu Leu Asn Glu Leu Glu Val Val Lys Ser Arg Val Lys Glu Leu Glu
465                 470                 475                 480

Cys Ser Glu Ser Arg Leu Glu Lys Ala Glu Leu Ser Leu Lys Asp Asp
                485                 490                 495

Leu Thr Lys Leu Lys Ser Phe Thr Val Met Leu Val Asp Glu Arg Lys
            500                 505                 510

Asn Met Met Glu Lys Ile Lys Gln Glu Glu Arg Lys Val Asp Gly Leu
        515                 520                 525

Asn Lys Asn Phe Lys Val Glu Gln Gly Lys Val Met Asp Val Thr Glu
    530                 535                 540

Lys Leu Ile Glu Glu Ser Lys Lys Leu Lys Leu Lys Ser Glu Met
545                 550                 555                 560

Glu Glu Lys Glu Tyr Ser Leu Thr Lys Glu Arg Asp Glu Leu Met Gly
                565                 570                 575

Lys Leu Arg Ser Glu Glu Glu Arg Ser Cys Glu Leu Ser Cys Ser Val
```

-continued

```
                580                 585                 590
Asp Leu Leu Lys Lys Arg Leu Asp Gly Ile Glu Glu Val Glu Arg Glu
            595                 600                 605
Ile Asn Arg Gly Arg Ser Cys Lys Gly Ser Glu Phe Thr Cys Pro Glu
        610                 615                 620
Asp Asn Lys Ile Arg Glu Leu Thr Leu Glu Ile Glu Arg Leu Lys Lys
625                 630                 635                 640
Arg Leu Gln Gln Leu Glu Val Val Glu Gly Asp Leu Met Lys Thr Glu
                645                 650                 655
Asp Glu Tyr Asp Gln Leu Glu Gln Lys Phe Arg Thr Glu Gln Asp Lys
            660                 665                 670
Ala Asn Phe Leu Ser Gln Gln Leu Glu Glu Ile Lys His Gln Met Ala
        675                 680                 685
Lys His Lys Ala Ile Glu Lys Gly Glu Ala Val Ser Gln Glu Ala Glu
    690                 695                 700
Leu Arg His Arg Phe Arg Leu Glu Glu Ala Lys Ser Arg Asp Leu Gln
705                 710                 715                 720
Ala Glu Val Gln Ala Leu Lys Glu Lys Ile His Glu Leu Met Asn Lys
                725                 730                 735
Glu Asp Gln Leu Ser Gln Leu Gln Val Asp Tyr Ser Val Leu Gln Gln
            740                 745                 750
Arg Phe Met Glu Glu Glu Thr Lys Asn Lys Asn Met Gly Arg Glu Val
        755                 760                 765
Leu Asn Leu Thr Lys Glu Leu Glu Leu Ser Lys Arg Tyr Ser Arg Ala
    770                 775                 780
Leu Arg Pro Ser Gly Asn Gly Arg Arg Met Val Asp Val Pro Val Ala
785                 790                 795                 800
Ser Thr Gly Val Gln Thr Glu Ala Val Cys Gly Asp Ala Ala Glu Glu
                805                 810                 815
Glu Thr Pro Ala Val Phe Ile Arg Lys Ser Phe Gln Glu Glu Asn His
            820                 825                 830
Ile Met Ser Asn Leu Arg Gln Val Gly Leu Lys Lys Pro Met Glu Arg
        835                 840                 845
Ser Ser Val Leu Asp Arg Tyr Pro Pro Ala Ala Asn Glu Leu Thr Met
    850                 855                 860
Arg Lys Ser Trp Ile Pro Trp Met Arg Lys Arg Glu Asn Gly Pro Ser
865                 870                 875                 880
Thr Pro Gln Glu Lys Gly Pro Arg Pro Asn Gln Gly Ala Gly His Pro
                885                 890                 895
Gly Glu Leu Val Leu Ala Pro Lys Gln Gly Gln Pro Leu His Ile Arg
            900                 905                 910
Val Thr Pro Asp His Glu Asn Ser Thr Ala Thr Leu Glu Ile Thr Ser
        915                 920                 925
Pro Thr Ser Glu Glu Phe Phe Ser Ser Thr Thr Val Ile Pro Thr Leu
    930                 935                 940
Gly Asn Gln Lys Pro Arg Ile Thr Ile Pro Ser Pro Asn Val Met
945                 950                 955                 960
Ser Gln Lys Pro Lys Ser Ala Asp Pro Thr Leu Gly Pro Glu Arg Ala
                965                 970                 975
Met Ser Pro Val Thr Ile Thr Ile Ser Arg Glu Lys Ser Pro Glu
            980                 985                 990
Gly Gly Arg Ser Ala Phe Ala Asp Arg Pro Ala Ser Pro Ile Gln Ile
        995                 1000                1005
```

-continued

```
Met Thr Val Ser Thr Ser Ala Ala Pro Thr Glu Ile Ala Val Ser Pro
    1010                1015                1020

Glu Ser Gln Glu Val Pro Met Gly Arg Thr Ile Leu Lys Val Thr Pro
1025                1030                1035                1040

Glu Lys Gln Thr Val Pro Ala Pro Val Arg Lys Tyr Asn Ser Asn Ala
                1045                1050                1055

Asn Ile Ile Thr Thr Glu Asp Asn Lys Ile His Ile His Leu Gly Ser
            1060                1065                1070

Gln Phe Lys Arg Ser Pro Gly Pro Ala Ala Glu Gly Val Ser Pro Val
        1075                1080                1085

Ile Thr Val Arg Pro Val Asn Val Thr Ala Glu Lys Glu Val Ser Thr
    1090                1095                1100

Gly Thr Val Leu Arg Ser Pro Arg Asn His Leu Ser Ser Arg Pro Gly
1105                1110                1115                1120

Ala Ser Lys Val Thr Ser Thr Ile Thr Ile Thr Pro Val Thr Thr Ser
                1125                1130                1135

Ser Thr Arg Gly Thr Gln Ser Val Ser Gly Gln Asp Gly Ser Ser Gln
            1140                1145                1150

Arg Pro Thr Pro Thr Arg Ile Pro Met Ser Lys Gly Met Lys Ala Gly
        1155                1160                1165

Lys Pro Val Val Ala Ala Ser Gly Ala Gly Asn Leu Thr Lys Phe Gln
    1170                1175                1180

Pro Arg Ala Glu Thr Gln Ser Met Lys Ile Glu Leu Lys Lys Ser Ala
1185                1190                1195                1200

Ala Ser Ser Thr Ala Ser Leu Gly Gly Gly Lys Gly
                1205                1210

<210> SEQ ID NO 3
<211> LENGTH: 3785
<212> TYPE: DNA
<213> ORGANISM: Rattus norvegicus
<220> FEATURE:
<221> NAME/KEY: CDS
<222> LOCATION: (237)..(3131)

<400> SEQUENCE: 3
cgacagggcc ggaatgtgcc tgttaatccc ctgtgaagta agaggttgag cagagcctgc      60
tgctgttgaa caaacttcag tacctcctta tttaaaaaaa aaaagacct agaaacaaaa      120 ggttgaaaaa gctccttgaa caagaaaaag cttaccaagc ccgcaaagaa aaggaaaacg      180
ctaagcggct caacaaactt cgagatgagc ttgtgaagct caagtccttc gccctc atg    239
                                                                 Met
                                                                  1 ttg gtg gac gag agg cag atg cac atc gag caa ctg ggc ctg cag agt      287
Leu Val Asp Glu Arg Gln Met His Ile Glu Gln Leu Gly Leu Gln Ser
    5                   10                  15 cag aaa gtc cag gac ctc act cag aag ctg agg gag gag gaa gaa aaa      335
Gln Lys Val Gln Asp Leu Thr Gln Lys Leu Arg Glu Glu Glu Glu Lys
20                  25                  30 ctc aaa gcg gtc act tac aaa tcc aag gaa gac cgc cag aag ctg ctc      383
Leu Lys Ala Val Thr Tyr Lys Ser Lys Glu Asp Arg Gln Lys Leu Leu
        35                  40                  45 aag tta gaa gtg gac ttc gaa cac aag gcc tcg agg ttt tcc cag gag      431
Lys Leu Glu Val Asp Phe Glu His Lys Ala Ser Arg Phe Ser Gln Glu
50                  55                  60                  65 cac gaa gag atg aac gcc aaa ttg gcg aat caa gaa tct cac aac cgg      479
His Glu Glu Met Asn Ala Lys Leu Ala Asn Gln Glu Ser His Asn Arg
```

|  |  |  |  |  |  |  |  |  |  |  |  |  |  |  |  |
|---|---|---|---|---|---|---|---|---|---|---|---|---|---|---|---|
|  |  | 70 |  |  |  |  | 75 |  |  |  |  | 80 |  |  |  |

```
caa ctt cga ctc aaa ctg gtt ggc tta tcg caa agg att gag gag ctg       527
Gln Leu Arg Leu Lys Leu Val Gly Leu Ser Gln Arg Ile Glu Glu Leu
            85                  90                  95 gaa gag acc aat aaa agc ctt cag aag gca gag gaa gag ctc cag gag       575
Glu Glu Thr Asn Lys Ser Leu Gln Lys Ala Glu Glu Glu Leu Gln Glu
                100                 105                 110 ctg aga gag aaa att gcc aaa ggg gaa tgt gga aac tcc agt ctc atg       623
Leu Arg Glu Lys Ile Ala Lys Gly Glu Cys Gly Asn Ser Ser Leu Met
        115                 120                 125 gcg gaa gtg gag agt ctg cgc aag cgc gtg ctt gag atg gag ggc aag       671
Ala Glu Val Glu Ser Leu Arg Lys Arg Val Leu Glu Met Glu Gly Lys
130                 135                 140                 145 gat gaa gag atc acg aag acc gag gcc cag tgc cgg gag ctg aag aag       719
Asp Glu Glu Ile Thr Lys Thr Glu Ala Gln Cys Arg Glu Leu Lys Lys
                150                 155                 160 aag ctc caa gag gaa gaa cac cac agc aag gaa ctt aga cta gaa gtg       767
Lys Leu Gln Glu Glu Glu His His Ser Lys Glu Leu Arg Leu Glu Val
            165                 170                 175 gag aag ctg cag aag agg atg tct gag ctg gag aag ctg gag gaa gcg       815
Glu Lys Leu Gln Lys Arg Met Ser Glu Leu Glu Lys Leu Glu Glu Ala
        180                 185                 190 ttc agc cgg agt aag tcg gaa tgc acc cag ctc cat ctg aac ctg gag       863
Phe Ser Arg Ser Lys Ser Glu Cys Thr Gln Leu His Leu Asn Leu Glu
    195                 200                 205 aag gag aag aac cta acc aaa gac ctg ctg aac gag ctg gag gtg gtc       911
Lys Glu Lys Asn Leu Thr Lys Asp Leu Leu Asn Glu Leu Glu Val Val
210                 215                 220                 225 aag agt cga gtt aaa gaa ctc gaa tgc tcc gag agt aga ctg gag aag       959
Lys Ser Arg Val Lys Glu Leu Glu Cys Ser Glu Ser Arg Leu Glu Lys
                230                 235                 240 gcc gag tta agc ctc aaa gat gac ctt aca aag ctg aag tcc ttc act      1007
Ala Glu Leu Ser Leu Lys Asp Asp Leu Thr Lys Leu Lys Ser Phe Thr
            245                 250                 255 gtg atg ctg gtg gat gag agg aaa aat atg atg gag aaa ata aag caa      1055
Val Met Leu Val Asp Glu Arg Lys Asn Met Met Glu Lys Ile Lys Gln
        260                 265                 270 gaa gag agg aaa gtg gat ggg ttg aat aaa aac ttt aag gtg gag cag      1103
Glu Glu Arg Lys Val Asp Gly Leu Asn Lys Asn Phe Lys Val Glu Gln
    275                 280                 285 gga aaa gtc atg gat gtg acg gaa aag cta atc gag gaa agc aag aag      1151
Gly Lys Val Met Asp Val Thr Glu Lys Leu Ile Glu Glu Ser Lys Lys
290                 295                 300                 305 ctt tta aaa ctc aaa tct gaa atg gag gaa aag gag tac agt ctg aca      1199
Leu Leu Lys Leu Lys Ser Glu Met Glu Glu Lys Glu Tyr Ser Leu Thr
                310                 315                 320 aag gag agg gat gag ctg atg ggt aaa ctg agg agc gaa gaa gaa agg      1247
Lys Glu Arg Asp Glu Leu Met Gly Lys Leu Arg Ser Glu Glu Glu Arg
            325                 330                 335 tcc tgt gaa ctg agc tgc agt gta gac tta cta aag aag cgg ctt gat      1295
Ser Cys Glu Leu Ser Cys Ser Val Asp Leu Leu Lys Lys Arg Leu Asp
        340                 345                 350 ggc ata gag gag gta gaa agg gaa ata aac cga ggt agg tcg tgc aag      1343
Gly Ile Glu Glu Val Glu Arg Glu Ile Asn Arg Gly Arg Ser Cys Lys
    355                 360                 365 ggg tct gag ttc acc tgc ccg gaa gac aat aag atc aga gaa cta acg      1391
Gly Ser Glu Phe Thr Cys Pro Glu Asp Asn Lys Ile Arg Glu Leu Thr
370                 375                 380                 385 ctt gaa atc gag aga ctg aag aaa cgg ctc cag cag ttg gag gtg gtg      1439
```

```
Leu Glu Ile Glu Arg Leu Lys Lys Arg Leu Gln Gln Leu Glu Val Val
            390                 395                 400 gag ggg gac ttg atg aag acc gag gac gaa tat gac cag ttg gag cag        1487
Glu Gly Asp Leu Met Lys Thr Glu Asp Glu Tyr Asp Gln Leu Glu Gln
            405                 410                 415 aag ttc aga acc gag cag gat aag gca aac ttc ctc tcc cag cag ctc        1535
Lys Phe Arg Thr Glu Gln Asp Lys Ala Asn Phe Leu Ser Gln Gln Leu
            420                 425                 430 gag gaa atc aaa cac caa atg gcc aag cac aaa gcc ata gag aaa ggg        1583
Glu Glu Ile Lys His Gln Met Ala Lys His Lys Ala Ile Glu Lys Gly
        435                 440                 445 gag gcc gtg agc cag gaa gcc gaa ctg cga cac agg ttt cgg ctg gag        1631
Glu Ala Val Ser Gln Glu Ala Glu Leu Arg His Arg Phe Arg Leu Glu
450                 455                 460                 465 gag gct aaa agt cgt gat tta cag gcc gag gtg cag gct ctc aag gag        1679
Glu Ala Lys Ser Arg Asp Leu Gln Ala Glu Val Gln Ala Leu Lys Glu
                470                 475                 480 aag atc cac gag ctg atg aac aag gaa gac cag ctg tct cag ctc caa        1727
Lys Ile His Glu Leu Met Asn Lys Glu Asp Gln Leu Ser Gln Leu Gln
            485                 490                 495 gtc gac tat tcg gtc ctt cag caa aga ttt atg gaa gaa gaa act aag        1775
Val Asp Tyr Ser Val Leu Gln Gln Arg Phe Met Glu Glu Glu Thr Lys
        500                 505                 510 aac aag aac atg ggg agg gag gtc ctc aat ctg acc aag gag cta gag        1823
Asn Lys Asn Met Gly Arg Glu Val Leu Asn Leu Thr Lys Glu Leu Glu
    515                 520                 525 ctt tcc aag cgc tac agc cga gct ctc agg ccg agt ggg aac ggc cga        1871
Leu Ser Lys Arg Tyr Ser Arg Ala Leu Arg Pro Ser Gly Asn Gly Arg
530                 535                 540                 545 agg atg gtg gac gtg cct gtg gcc tcc act ggg gtg cag acc gag gcg        1919
Arg Met Val Asp Val Pro Val Ala Ser Thr Gly Val Gln Thr Glu Ala
                550                 555                 560 gtg tgc ggg gat gct gcg gag gag gag acc ccg gct gtg ttc att cgc        1967
Val Cys Gly Asp Ala Ala Glu Glu Glu Thr Pro Ala Val Phe Ile Arg
            565                 570                 575 aaa tcc ttc cag gag gaa aat cac atc atg agt aat ctt cga cag gta        2015
Lys Ser Phe Gln Glu Glu Asn His Ile Met Ser Asn Leu Arg Gln Val
        580                 585                 590 ggc ctg aag aaa ccc atg gaa cgg tcc tcg gtc ctc gac agg tat ccc        2063
Gly Leu Lys Lys Pro Met Glu Arg Ser Ser Val Leu Asp Arg Tyr Pro
    595                 600                 605 cca gca gcg aat gag ctc acc atg agg aag tct tgg att cct tgg atg        2111
Pro Ala Ala Asn Glu Leu Thr Met Arg Lys Ser Trp Ile Pro Trp Met
610                 615                 620                 625 aga aaa aga gaa aac ggt cct tcc act ccg cag gag aaa ggg ccc agg        2159
Arg Lys Arg Glu Asn Gly Pro Ser Thr Pro Gln Glu Lys Gly Pro Arg
                630                 635                 640 cca aac cag ggt gca ggg cac ccc ggg gag ctg gtc cta gca cca aag        2207
Pro Asn Gln Gly Ala Gly His Pro Gly Glu Leu Val Leu Ala Pro Lys
            645                 650                 655 cag ggc cag ccc cta cac atc cgt gtg aca cca gat cat gag aac agc        2255
Gln Gly Gln Pro Leu His Ile Arg Val Thr Pro Asp His Glu Asn Ser
        660                 665                 670 act gcc acc ctg gag atc aca agc ccc aca tct gaa gag ttt ttc tct        2303
Thr Ala Thr Leu Glu Ile Thr Ser Pro Thr Ser Glu Glu Phe Phe Ser
    675                 680                 685 agt acc acc gtc att cct acc tta ggc aac cag aaa cca aga ata acc        2351
Ser Thr Thr Val Ile Pro Thr Leu Gly Asn Gln Lys Pro Arg Ile Thr
690                 695                 700                 705
```

```
att att cca tca ccc aat gtc atg tcg caa aag ccc aaa agt gca gat    2399
Ile Ile Pro Ser Pro Asn Val Met Ser Gln Lys Pro Lys Ser Ala Asp
            710                 715                 720 cct act ctc ggc cca gaa cga gcc atg tcc cct gtc acg att act act    2447
Pro Thr Leu Gly Pro Glu Arg Ala Met Ser Pro Val Thr Ile Thr Thr
        725                 730                 735 att tcc aga gag aag agc ccg gaa ggt gga agg agc gcc ttt gcc gac    2495
Ile Ser Arg Glu Lys Ser Pro Glu Gly Gly Arg Ser Ala Phe Ala Asp
        740                 745                 750 agg cct gca tcc ccc atc caa atc atg acg gtg tca aca tct gca gct    2543
Arg Pro Ala Ser Pro Ile Gln Ile Met Thr Val Ser Thr Ser Ala Ala
    755                 760                 765 ccc act gaa atc gct gtc tct cct gaa tct cag gaa gtg cct atg gga    2591
Pro Thr Glu Ile Ala Val Ser Pro Glu Ser Gln Glu Val Pro Met Gly
770                 775                 780                 785 agg act atc ctc aaa gtc acc ccg gaa aaa caa act gtt cca gcc ccc    2639
Arg Thr Ile Leu Lys Val Thr Pro Glu Lys Gln Thr Val Pro Ala Pro
            790                 795                 800 gtg cgg aag tac aac tcc aat gct aat atc atc acc acg gaa gac aat    2687
Val Arg Lys Tyr Asn Ser Asn Ala Asn Ile Ile Thr Thr Glu Asp Asn
        805                 810                 815 aaa att cac att cac ctg ggt tct cag ttt aag cga tct cct ggg cct    2735
Lys Ile His Ile His Leu Gly Ser Gln Phe Lys Arg Ser Pro Gly Pro
        820                 825                 830 gcc gct gaa ggc gtg agc cca gtt atc acc gtc cgg cct gtc aac gtg    2783
Ala Ala Glu Gly Val Ser Pro Val Ile Thr Val Arg Pro Val Asn Val
    835                 840                 845 aca gcg gag aag gag gtt tct aca ggc aca gtc ctt cgc tct ccc agg    2831
Thr Ala Glu Lys Glu Val Ser Thr Gly Thr Val Leu Arg Ser Pro Arg
850                 855                 860                 865 aac cac ctc tct tca aga ccc ggt gct agc aaa gtg acc agc act ata    2879
Asn His Leu Ser Ser Arg Pro Gly Ala Ser Lys Val Thr Ser Thr Ile
            870                 875                 880 act ata acc ccg gtc aca acg tca tcc aca cga gga acc caa tca gtg    2927
Thr Ile Thr Pro Val Thr Thr Ser Ser Thr Arg Gly Thr Gln Ser Val
        885                 890                 895 tca gga caa gat ggg tca tct cag cgg cct acc ccc acc cgc att cct    2975
Ser Gly Gln Asp Gly Ser Ser Gln Arg Pro Thr Pro Thr Arg Ile Pro
        900                 905                 910 atg tca aaa ggt atg aaa gct gga aag cca gta gtg gca gcc tca gga    3023
Met Ser Lys Gly Met Lys Ala Gly Lys Pro Val Val Ala Ala Ser Gly
    915                 920                 925 gca gga aat ctg acc aaa ttc cag cct cga gct gag act cag tct atg    3071
Ala Gly Asn Leu Thr Lys Phe Gln Pro Arg Ala Glu Thr Gln Ser Met
930                 935                 940                 945 aaa ata gag ctg aag aaa tct gca gcc agc agc act gcc tct ctt gga    3119
Lys Ile Glu Leu Lys Lys Ser Ala Ala Ser Ser Thr Ala Ser Leu Gly
            950                 955                 960 ggg ggg aag ggc tgagggcagt ggctaagggg gtatgttgta aggatgctac        3171
Gly Gly Lys Gly
            965 tgctgcagtg gaaacaaacc ttcctctgtg ccaacccttt ccttgtacta ctaatttaag  3231 ttttaaatat cttgtttata aaataaccat ttaatagcca tgcacccccc tcccattttg  3291 tgcatctgtt tcaatgcagg ggaatagaat taattagcag aatttctgtt tgctgaatgt  3351 tctgttgaag atgttggtcc agttcagttt tacttctagc atgtggcccc attcaaggta  3411 gctcacgagt tgtgaagccc tcaatatcgt caccggagag atttgaggac cacattacat  3471 atgctcccaa aggctggctc ccaattttcc taattgtaag ccaactttaa tagactcagt  3531
```

-continued

```
tctgtgattt ttttttccaa aaaaaaaata ttttgaaata ggacagagtt taacagttgt    3591
cattttgcac tatcaagcca tgagtttgat atatgggtta taagaaaaga atactttcag    3651
agctatcaca gggtctctaa acttttggaa aaacaaaagc ccctaatatg acctcaggaa    3711
acaatttgaa catgaaataa aatggaaatg aactgtggaa tcttaaaaaa aaaaaaaaaa    3771
aaaaaaaaaa aaaa                                                      3785
```

<210> SEQ ID NO 4
<211> LENGTH: 965
<212> TYPE: PRT
<213> ORGANISM: Rattus norvegicus

<400> SEQUENCE: 4

```
Met Leu Val Asp Glu Arg Gln Met His Ile Glu Gln Leu Gly Leu Gln
 1               5                  10                  15

Ser Gln Lys Val Gln Asp Leu Thr Gln Lys Leu Arg Glu Glu Glu Glu
             20                  25                  30

Lys Leu Lys Ala Val Thr Tyr Lys Ser Lys Glu Asp Arg Gln Lys Leu
         35                  40                  45

Leu Lys Leu Glu Val Asp Phe Glu His Lys Ala Ser Arg Phe Ser Gln
     50                  55                  60

Glu His Glu Glu Met Asn Ala Lys Leu Ala Asn Gln Glu Ser His Asn
 65                  70                  75                  80

Arg Gln Leu Arg Leu Lys Leu Val Gly Leu Ser Gln Arg Ile Glu Glu
                 85                  90                  95

Leu Glu Glu Thr Asn Lys Ser Leu Gln Lys Ala Glu Glu Glu Leu Gln
            100                 105                 110

Glu Leu Arg Glu Lys Ile Ala Lys Gly Glu Cys Gly Asn Ser Ser Leu
        115                 120                 125

Met Ala Glu Val Glu Ser Leu Arg Lys Arg Val Leu Glu Met Glu Gly
    130                 135                 140

Lys Asp Glu Glu Ile Thr Lys Thr Glu Ala Gln Cys Arg Glu Leu Lys
145                 150                 155                 160

Lys Lys Leu Gln Glu Glu His His Ser Lys Glu Leu Arg Leu Glu
                165                 170                 175

Val Glu Lys Leu Gln Lys Arg Met Ser Glu Leu Glu Lys Leu Glu Glu
            180                 185                 190

Ala Phe Ser Arg Ser Lys Ser Glu Cys Thr Gln Leu His Leu Asn Leu
        195                 200                 205

Glu Lys Glu Lys Asn Leu Thr Lys Asp Leu Leu Asn Glu Leu Glu Val
    210                 215                 220

Val Lys Ser Arg Val Lys Glu Leu Glu Cys Ser Glu Ser Arg Leu Glu
225                 230                 235                 240

Lys Ala Glu Leu Ser Leu Lys Asp Asp Leu Thr Lys Leu Lys Ser Phe
                245                 250                 255

Thr Val Met Leu Val Asp Glu Arg Lys Asn Met Met Glu Lys Ile Lys
            260                 265                 270

Gln Glu Glu Arg Lys Val Asp Gly Leu Asn Lys Asn Phe Lys Val Glu
        275                 280                 285

Gln Gly Lys Val Met Asp Val Thr Glu Lys Leu Ile Glu Glu Ser Lys
    290                 295                 300

Lys Leu Leu Lys Leu Lys Ser Glu Met Glu Glu Lys Glu Tyr Ser Leu
305                 310                 315                 320
```

-continued

```
Thr Lys Glu Arg Asp Glu Leu Met Gly Lys Leu Arg Ser Glu Glu
                325                 330                 335

Arg Ser Cys Glu Leu Ser Cys Ser Val Asp Leu Leu Lys Lys Arg Leu
                340                 345                 350

Asp Gly Ile Glu Val Glu Arg Glu Ile Asn Arg Gly Arg Ser Cys
                355                 360                 365

Lys Gly Ser Glu Phe Thr Cys Pro Asp Asn Lys Ile Arg Glu Leu
                370                 375                 380

Thr Leu Glu Ile Glu Arg Leu Lys Lys Arg Leu Gln Gln Leu Glu Val
385                 390                 395                 400

Val Glu Gly Asp Leu Met Lys Thr Glu Asp Glu Tyr Asp Gln Leu Glu
                405                 410                 415

Gln Lys Phe Arg Thr Glu Gln Asp Lys Ala Asn Phe Leu Ser Gln Gln
                420                 425                 430

Leu Glu Glu Ile Lys His Gln Met Ala Lys His Lys Ala Ile Glu Lys
                435                 440                 445

Gly Glu Ala Val Ser Gln Glu Ala Glu Leu Arg His Arg Phe Arg Leu
                450                 455                 460

Glu Glu Ala Lys Ser Arg Asp Leu Gln Ala Glu Val Gln Ala Leu Lys
465                 470                 475                 480

Glu Lys Ile His Glu Leu Met Asn Lys Glu Asp Gln Leu Ser Gln Leu
                485                 490                 495

Gln Val Asp Tyr Ser Val Leu Gln Gln Arg Phe Met Glu Glu Glu Thr
                500                 505                 510

Lys Asn Lys Asn Met Gly Arg Glu Val Leu Asn Leu Thr Lys Glu Leu
                515                 520                 525

Glu Leu Ser Lys Arg Tyr Ser Arg Ala Leu Arg Pro Ser Gly Asn Gly
                530                 535                 540

Arg Arg Met Val Asp Val Pro Val Ala Ser Thr Gly Val Gln Thr Glu
545                 550                 555                 560

Ala Val Cys Gly Asp Ala Ala Glu Glu Glu Thr Pro Ala Val Phe Ile
                565                 570                 575

Arg Lys Ser Phe Gln Glu Glu Asn His Ile Met Ser Asn Leu Arg Gln
                580                 585                 590

Val Gly Leu Lys Lys Pro Met Glu Arg Ser Ser Val Leu Asp Arg Tyr
                595                 600                 605

Pro Pro Ala Ala Asn Glu Leu Thr Met Arg Lys Ser Trp Ile Pro Trp
                610                 615                 620

Met Arg Lys Arg Glu Asn Gly Pro Ser Thr Pro Gln Glu Lys Gly Pro
625                 630                 635                 640

Arg Pro Asn Gln Gly Ala Gly His Pro Gly Glu Leu Val Leu Ala Pro
                645                 650                 655

Lys Gln Gly Gln Pro Leu His Ile Arg Val Thr Pro Asp His Glu Asn
                660                 665                 670

Ser Thr Ala Thr Leu Glu Ile Thr Ser Pro Thr Ser Glu Glu Phe Phe
                675                 680                 685

Ser Ser Thr Thr Val Ile Pro Thr Leu Gly Asn Gln Lys Pro Arg Ile
                690                 695                 700

Thr Ile Ile Pro Ser Pro Asn Val Met Ser Gln Lys Pro Lys Ser Ala
705                 710                 715                 720

Asp Pro Thr Leu Gly Pro Glu Arg Ala Met Ser Pro Val Thr Ile Thr
                725                 730                 735

Thr Ile Ser Arg Glu Lys Ser Pro Glu Gly Gly Arg Ser Ala Phe Ala
```

-continued

```
                740                 745                 750
Asp Arg Pro Ala Ser Pro Ile Gln Ile Met Thr Val Ser Thr Ser Ala
        755                 760                 765
Ala Pro Thr Glu Ile Ala Val Ser Pro Glu Ser Gln Glu Val Pro Met
        770                 775                 780
Gly Arg Thr Ile Leu Lys Val Thr Pro Glu Lys Gln Thr Val Pro Ala
785                 790                 795                 800
Pro Val Arg Lys Tyr Asn Ser Asn Ala Asn Ile Ile Thr Thr Glu Asp
                805                 810                 815
Asn Lys Ile His Ile His Leu Gly Ser Gln Phe Lys Arg Ser Pro Gly
                820                 825                 830
Pro Ala Ala Glu Gly Val Ser Pro Val Ile Thr Val Arg Pro Val Asn
                835                 840                 845
Val Thr Ala Glu Lys Glu Val Ser Thr Gly Thr Val Leu Arg Ser Pro
        850                 855                 860
Arg Asn His Leu Ser Ser Arg Pro Gly Ala Ser Lys Val Thr Ser Thr
865                 870                 875                 880
Ile Thr Ile Thr Pro Val Thr Thr Ser Ser Thr Arg Gly Thr Gln Ser
                885                 890                 895
Val Ser Gly Gln Asp Gly Ser Ser Gln Arg Pro Thr Pro Thr Arg Ile
                900                 905                 910
Pro Met Ser Lys Gly Met Lys Ala Gly Lys Pro Val Val Ala Ala Ser
                915                 920                 925
Gly Ala Gly Asn Leu Thr Lys Phe Gln Pro Arg Ala Glu Thr Gln Ser
        930                 935                 940
Met Lys Ile Glu Leu Lys Lys Ser Ala Ala Ser Ser Thr Ala Ser Leu
945                 950                 955                 960
Gly Gly Gly Lys Gly
                965

<210> SEQ ID NO 5
<211> LENGTH: 4247
<212> TYPE: DNA
<213> ORGANISM: Homo sapiens
<220> FEATURE:
<221> NAME/KEY: CDS
<222> LOCATION: (7)..(3645)

<400> SEQUENCE: 5 gtggga atg aga tct cga aac caa ggt ggt gaa agt gca tct gat ggg          48
       Met Arg Ser Arg Asn Gln Gly Gly Glu Ser Ala Ser Asp Gly
         1               5                  10 cat atc tcc tgt ccc aag ccc tcc atc atc ggc aat gct ggt gaa aaa        96
His Ile Ser Cys Pro Lys Pro Ser Ile Ile Gly Asn Ala Gly Glu Lys
 15                  20                  25                  30 agt ctc tca gaa gat gca aaa aag aag aag aaa tca aat agg aag gag       144
Ser Leu Ser Glu Asp Ala Lys Lys Lys Lys Lys Ser Asn Arg Lys Glu
                 35                  40                  45 gat gat gtc atg gcc tca gga act gtc aaa cga cac cta aaa aca tct       192
Asp Asp Val Met Ala Ser Gly Thr Val Lys Arg His Leu Lys Thr Ser
             50                  55                  60 gga gaa tgt gaa cga aaa act aag aaa tcc ctg gag tta tcc aaa gaa       240
Gly Glu Cys Glu Arg Lys Thr Lys Lys Ser Leu Glu Leu Ser Lys Glu
         65                  70                  75 gac ctc atc caa cta ctc agt ata atg gaa ggg gag ttg cag gcc aga       288
Asp Leu Ile Gln Leu Leu Ser Ile Met Glu Gly Glu Leu Gln Ala Arg
     80                  85                  90
```

-continued

| | |
|---|---|
| gaa gat gtg atc cac atg ctg aag aca gag aaa acc aag cct gag gtt<br>Glu Asp Val Ile His Met Leu Lys Thr Glu Lys Thr Lys Pro Glu Val<br>95                      100                   105                 110 | 336 |
| ctg gag gct cat tac ggg tct gcg gag cca gag aaa gtg ctg cgg gtc<br>Leu Glu Ala His Tyr Gly Ser Ala Glu Pro Glu Lys Val Leu Arg Val<br>                  115                   120                 125 | 384 |
| ctg cac cga gat gcc att ctt gcc cag gag aaa tcc ata gga gaa gat<br>Leu His Arg Asp Ala Ile Leu Ala Gln Glu Lys Ser Ile Gly Glu Asp<br>            130                   135                 140 | 432 |
| gtc tat gag aaa ccg att tca gag ctg gac aga ctt gag gaa aaa cag<br>Val Tyr Glu Lys Pro Ile Ser Glu Leu Asp Arg Leu Glu Glu Lys Gln<br>145                     150                   155 | 480 |
| aaa gaa acc tac cgg cgc atg cta gag cag ctg ttg ctg gcc gag aag<br>Lys Glu Thr Tyr Arg Arg Met Leu Glu Gln Leu Leu Leu Ala Glu Lys<br>            160                   165                 170 | 528 |
| tgt cat agg cgc acc gta tac gag tta gag aac gag aag cat aaa cac<br>Cys His Arg Arg Thr Val Tyr Glu Leu Glu Asn Glu Lys His Lys His<br>175                     180                   185                 190 | 576 |
| act gac tac atg aac aag agc gac gac ttc acc aac ctg ctg gag cag<br>Thr Asp Tyr Met Asn Lys Ser Asp Asp Phe Thr Asn Leu Leu Glu Gln<br>                      195                   200                 205 | 624 |
| gag cgg gag agg tta aaa aag ctc ctt gaa caa gaa aag gct tat caa<br>Glu Arg Glu Arg Leu Lys Lys Leu Leu Glu Gln Glu Lys Ala Tyr Gln<br>            210                   215                 220 | 672 |
| gcc cgc aaa gaa aag gaa aat gct aaa cga ctc aat aaa cta aga gat<br>Ala Arg Lys Glu Lys Glu Asn Ala Lys Arg Leu Asn Lys Leu Arg Asp<br>225                     230                   235 | 720 |
| gag ctt gtt aaa ctc aaa tcc ttt gca ctc atg ctg gtg gat gaa aga<br>Glu Leu Val Lys Leu Lys Ser Phe Ala Leu Met Leu Val Asp Glu Arg<br>            240                   245                 250 | 768 |
| caa atg cac att gaa caa ctt ggc ctg caa agc cag aaa gta cag gat<br>Gln Met His Ile Glu Gln Leu Gly Leu Gln Ser Gln Lys Val Gln Asp<br>255                     260                   265                 270 | 816 |
| ctt act cag aag ctg agg gaa gaa gaa gag aag ctc aaa gcc att act<br>Leu Thr Gln Lys Leu Arg Glu Glu Glu Glu Lys Leu Lys Ala Ile Thr<br>                    275                   280                 285 | 864 |
| tcc aaa tcc aaa gaa gac aga cag aaa ttg ctc aag tta gaa gtg gac<br>Ser Lys Ser Lys Glu Asp Arg Gln Lys Leu Leu Lys Leu Glu Val Asp<br>            290                   295                 300 | 912 |
| ttt gaa cac aag gct tcg agg ttt tct caa gag cat gaa gag atg aac<br>Phe Glu His Lys Ala Ser Arg Phe Ser Gln Glu His Glu Glu Met Asn<br>                    305                   310                 315 | 960 |
| gct aaa ctg gct aat caa gag tct cac aat agg caa ctt aga ctc aag<br>Ala Lys Leu Ala Asn Gln Glu Ser His Asn Arg Gln Leu Arg Leu Lys<br>320                     325                   330 | 1008 |
| ctg gtt ggc tta acc caa aga atc gag gag cta gaa gag acc aac aaa<br>Leu Val Gly Leu Thr Gln Arg Ile Glu Glu Leu Glu Glu Thr Asn Lys<br>335                     340                   345                 350 | 1056 |
| aat ctg cag aag gca gag gaa gaa ctt caa gaa tta aga gat aaa att<br>Asn Leu Gln Lys Ala Glu Glu Glu Leu Gln Glu Leu Arg Asp Lys Ile<br>                    355                   360                 365 | 1104 |
| gcc aaa gga gaa tgt gga aac tct agc ctc atg gca gaa gtg gaa aat<br>Ala Lys Gly Glu Cys Gly Asn Ser Ser Leu Met Ala Glu Val Glu Asn<br>            370                   375                 380 | 1152 |
| ctt cga aag cgt gtg ctt gaa atg gaa ggt aaa gat gag gag atc act<br>Leu Arg Lys Arg Val Leu Glu Met Glu Gly Lys Asp Glu Glu Ile Thr<br>385                     390                   395 | 1200 |
| aaa act gaa tcc cag tgt agg gaa ttg agg aag aag ctg caa gag gaa<br>Lys Thr Glu Ser Gln Cys Arg Glu Leu Arg Lys Lys Leu Gln Glu Glu<br>            400                   405                 410 | 1248 |

| | |
|---|---|
| gaa cac cat agt aag gag ctc aga ctt gaa gtt gag aag cta cag aag<br>Glu His His Ser Lys Glu Leu Arg Leu Glu Val Glu Lys Leu Gln Lys<br>415                     420                       425                    430 | 1296 |
| aga atg tct gaa cta gag aaa ttg gaa gaa gca ttt agc aag agt aaa<br>Arg Met Ser Glu Leu Glu Lys Leu Glu Glu Ala Phe Ser Lys Ser Lys<br>                   435                     440                       445 | 1344 |
| tct gag tgc acc cag cta cat tta aat ctg gag aaa gaa aag aac tta<br>Ser Glu Cys Thr Gln Leu His Leu Asn Leu Glu Lys Glu Lys Asn Leu<br>           450                     455                     460 | 1392 |
| acc aaa gac ctg cta aat gaa ttg gag gtg gtc aag agt cga gtt aaa<br>Thr Lys Asp Leu Leu Asn Glu Leu Glu Val Val Lys Ser Arg Val Lys<br>               465                     470                     475 | 1440 |
| gaa ttg gaa tgt tct gaa agt aga ttg gaa aag gct gaa tta agc cta<br>Glu Leu Glu Cys Ser Glu Ser Arg Leu Glu Lys Ala Glu Leu Ser Leu<br>480                     485                       490 | 1488 |
| aaa gat gat ctt acc aag ttg aag tca ttt acc gtg atg ctg gtt gat<br>Lys Asp Asp Leu Thr Lys Leu Lys Ser Phe Thr Val Met Leu Val Asp<br>495                     500                     505                    510 | 1536 |
| gaa agg aaa aat atg atg gaa aaa ata aaa caa gaa gag aga aaa gtg<br>Glu Arg Lys Asn Met Met Glu Lys Ile Lys Gln Glu Glu Arg Lys Val<br>                   515                     520                       525 | 1584 |
| gat gga ctc aat aaa aat ttt aag gtg gaa caa gga aaa gtt atg gat<br>Asp Gly Leu Asn Lys Asn Phe Lys Val Glu Gln Gly Lys Val Met Asp<br>           530                     535                     540 | 1632 |
| gta act gaa aaa cta att gaa gaa agt aag aaa ctt tta aaa cta aaa<br>Val Thr Glu Lys Leu Ile Glu Glu Ser Lys Lys Leu Leu Lys Leu Lys<br>               545                     550                     555 | 1680 |
| tct gaa atg gag gaa aaa gta tac aac ttg aca aga gaa aga gat gag<br>Ser Glu Met Glu Glu Lys Val Tyr Asn Leu Thr Arg Glu Arg Asp Glu<br>560                     565                       570 | 1728 |
| ttg ata ggc aaa ttg aaa agt gaa gaa gaa aaa tcc tct gaa tta agc<br>Leu Ile Gly Lys Leu Lys Ser Glu Glu Glu Lys Ser Ser Glu Leu Ser<br>575                     580                     585                    590 | 1776 |
| tgc agt gtt gac tta cta aag aag aga ctt gat ggt ata gag gaa gtg<br>Cys Ser Val Asp Leu Leu Lys Lys Arg Leu Asp Gly Ile Glu Glu Val<br>               595                     600                    605 | 1824 |
| gaa aga gaa ata aca aga gga agg tca cga aaa ggg tct gag ctc acc<br>Glu Arg Glu Ile Thr Arg Gly Arg Ser Arg Lys Gly Ser Glu Leu Thr<br>           610                     615                    620 | 1872 |
| tgc ccg gaa gat aat aag att aag gaa cta aca ctt gaa att gag aga<br>Cys Pro Glu Asp Asn Lys Ile Lys Glu Leu Thr Leu Glu Ile Glu Arg<br>               625                     630                    635 | 1920 |
| ctg aag aaa cgt ctc caa caa ttg gaa gtg gtc gaa ggg gat ttg atg<br>Leu Lys Lys Arg Leu Gln Gln Leu Glu Val Val Glu Gly Asp Leu Met<br>640                     645                     650 | 1968 |
| aag aca gaa gat gag tat gat cag ctg gaa cag aaa ttt aga act gag<br>Lys Thr Glu Asp Glu Tyr Asp Gln Leu Glu Gln Lys Phe Arg Thr Glu<br>655                     660                     665                    670 | 2016 |
| cag gat aag gct aac ttc ctc tct caa caa cta gag gag atc aag cac<br>Gln Asp Lys Ala Asn Phe Leu Ser Gln Gln Leu Glu Glu Ile Lys His<br>               675                     680                    685 | 2064 |
| caa att gcc aag aat aaa gca ata gag aag ggt gag gtt gtg agc cag<br>Gln Ile Ala Lys Asn Lys Ala Ile Glu Lys Gly Glu Val Val Ser Gln<br>           690                     695                    700 | 2112 |
| gaa gct gaa ctg aga cac aga ttt cgg ttg gaa gaa gct aaa agt cga<br>Glu Ala Glu Leu Arg His Arg Phe Arg Leu Glu Glu Ala Lys Ser Arg<br>               705                     710                    715 | 2160 |
| gac tta aaa gcc gaa gta caa gct ctt aaa gag aag att cac gaa tta<br>Asp Leu Lys Ala Glu Val Gln Ala Leu Lys Glu Lys Ile His Glu Leu | 2208 |

-continued

|  |  |  |  |  |  |  |  |  |  |  |  |  |  |  |  |
|---|---|---|---|---|---|---|---|---|---|---|---|---|---|---|---|
|  |  | 720 |  |  |  | 725 |  |  |  | 730 |  |  |  |  |  |
| atg | aac | aaa | gaa | gat | cag | ctt | tct | cag | ctc | cag | gta | gat | tat | tct | gta | 2256 |
| Met | Asn | Lys | Glu | Asp | Gln | Leu | Ser | Gln | Leu | Gln | Val | Asp | Tyr | Ser | Val |  |
| 735 |  |  |  | 740 |  |  |  |  | 745 |  |  |  |  | 750 |  |  |
| ctt | caa | caa | aga | ttt | atg | gaa | gaa | gaa | aat | aag | aac | aaa | aac | atg | ggg | 2304 |
| Leu | Gln | Gln | Arg | Phe | Met | Glu | Glu | Glu | Asn | Lys | Asn | Lys | Asn | Met | Gly |  |
|  |  |  |  |  | 755 |  |  |  |  | 760 |  |  |  |  | 765 |  |
| cag | gag | gtt | ctc | aat | ctg | acc | aaa | gag | ttg | gag | ctt | tcc | aag | cgc | tac | 2352 |
| Gln | Glu | Val | Leu | Asn | Leu | Thr | Lys | Glu | Leu | Glu | Leu | Ser | Lys | Arg | Tyr |  |
|  |  | 770 |  |  |  |  | 775 |  |  |  |  | 780 |  |  |  |  |
| agc | aga | gct | ctt | agg | ccc | agt | gtg | aat | gga | aga | aga | atg | gtg | gat | gtt | 2400 |
| Ser | Arg | Ala | Leu | Arg | Pro | Ser | Val | Asn | Gly | Arg | Arg | Met | Val | Asp | Val |  |
| 785 |  |  |  |  | 790 |  |  |  |  | 795 |  |  |  |  |  |  |
| cct | gtg | acg | tca | act | gga | gtc | caa | act | gat | gca | gtc | agc | ggt | gaa | gca | 2448 |
| Pro | Val | Thr | Ser | Thr | Gly | Val | Gln | Thr | Asp | Ala | Val | Ser | Gly | Glu | Ala |  |
| 800 |  |  |  |  | 805 |  |  |  |  | 810 |  |  |  |  |  |  |
| gca | gag | gaa | gaa | acg | cca | gct | gta | ttc | ata | cgg | aaa | tcc | ttc | cag | gaa | 2496 |
| Ala | Glu | Glu | Glu | Thr | Pro | Ala | Val | Phe | Ile | Arg | Lys | Ser | Phe | Gln | Glu |  |
| 815 |  |  |  | 820 |  |  |  |  | 825 |  |  |  |  | 830 |  |  |
| gaa | aat | cat | att | atg | agt | aat | ctt | cgg | cag | gtg | gga | ttg | aag | aaa | ccc | 2544 |
| Glu | Asn | His | Ile | Met | Ser | Asn | Leu | Arg | Gln | Val | Gly | Leu | Lys | Lys | Pro |  |
|  |  |  |  | 835 |  |  |  |  | 840 |  |  |  |  | 845 |  |  |
| gtg | gaa | aga | tct | tct | gtt | cta | gac | agg | tat | cct | cca | gca | gca | aat | gag | 2592 |
| Val | Glu | Arg | Ser | Ser | Val | Leu | Asp | Arg | Tyr | Pro | Pro | Ala | Ala | Asn | Glu |  |
|  |  | 850 |  |  |  |  | 855 |  |  |  |  | 860 |  |  |  |  |
| ctc | act | atg | aga | aag | tct | tgg | att | cca | tgg | atg | aga | aag | agg | gaa | aac | 2640 |
| Leu | Thr | Met | Arg | Lys | Ser | Trp | Ile | Pro | Trp | Met | Arg | Lys | Arg | Glu | Asn |  |
| 865 |  |  |  |  | 870 |  |  |  |  | 875 |  |  |  |  |  |  |
| ggc | ccc | tcc | atc | act | cag | gag | aaa | ggg | ccc | cga | aca | aat | tcc | agt | cca | 2688 |
| Gly | Pro | Ser | Ile | Thr | Gln | Glu | Lys | Gly | Pro | Arg | Thr | Asn | Ser | Ser | Pro |  |
| 880 |  |  |  |  | 885 |  |  |  |  | 890 |  |  |  |  |  |  |
| ggg | cac | cca | gga | gag | gta | gtc | ctt | tca | cca | aag | cag | ggc | cag | ccc | ctg | 2736 |
| Gly | His | Pro | Gly | Glu | Val | Val | Leu | Ser | Pro | Lys | Gln | Gly | Gln | Pro | Leu |  |
| 895 |  |  |  | 900 |  |  |  |  | 905 |  |  |  |  | 910 |  |  |
| cat | att | cga | gtg | aca | cca | gac | cac | gag | aac | agc | act | gcg | act | ttg | gag | 2784 |
| His | Ile | Arg | Val | Thr | Pro | Asp | His | Glu | Asn | Ser | Thr | Ala | Thr | Leu | Glu |  |
|  |  |  |  | 915 |  |  |  |  | 920 |  |  |  |  | 925 |  |  |
| ata | aca | agc | ccg | aca | tct | gaa | gaa | ttt | ttt | tct | agt | acc | act | gtc | att | 2832 |
| Ile | Thr | Ser | Pro | Thr | Ser | Glu | Glu | Phe | Phe | Ser | Ser | Thr | Thr | Val | Ile |  |
|  |  |  | 930 |  |  |  |  | 935 |  |  |  |  | 940 |  |  |  |
| cct | acc | tta | ggg | aat | cag | aaa | cca | aga | ata | acc | att | att | cca | tca | cca | 2880 |
| Pro | Thr | Leu | Gly | Asn | Gln | Lys | Pro | Arg | Ile | Thr | Ile | Ile | Pro | Ser | Pro |  |
| 945 |  |  |  |  | 950 |  |  |  |  | 955 |  |  |  |  |  |  |
| aac | gtt | atg | cct | caa | aaa | caa | aaa | agt | gga | gat | act | act | ctt | ggc | cca | 2928 |
| Asn | Val | Met | Pro | Gln | Lys | Gln | Lys | Ser | Gly | Asp | Thr | Thr | Leu | Gly | Pro |  |
| 960 |  |  |  |  | 965 |  |  |  |  | 970 |  |  |  |  |  |  |
| gaa | cga | gcc | atg | tcc | cca | gtc | aca | att | act | aca | ttt | tcc | aga | gag | aag | 2976 |
| Glu | Arg | Ala | Met | Ser | Pro | Val | Thr | Ile | Thr | Thr | Phe | Ser | Arg | Glu | Lys |  |
| 975 |  |  |  | 980 |  |  |  |  | 985 |  |  |  |  | 990 |  |  |
| act | cca | gaa | agt | gga | aga | ggc | gca | ttt | gca | gac | agg | ccc | aca | tcc | cct | 3024 |
| Thr | Pro | Glu | Ser | Gly | Arg | Gly | Ala | Phe | Ala | Asp | Arg | Pro | Thr | Ser | Pro |  |
|  |  |  |  | 995 |  |  |  |  | 1000 |  |  |  |  | 1005 |  |  |
| att | cag | ata | atg | acg | gtg | tct | aca | tca | gca | gca | cca | gct | gag | att | gca | 3072 |
| Ile | Gln | Ile | Met | Thr | Val | Ser | Thr | Ser | Ala | Ala | Pro | Ala | Glu | Ile | Ala |  |
|  |  |  | 1010 |  |  |  |  | 1015 |  |  |  |  | 1020 |  |  |  |
| gtt | tct | ccc | gaa | tcc | cag | gaa | atg | ccc | atg | gga | cgg | aca | atc | ctc | aaa | 3120 |
| Val | Ser | Pro | Glu | Ser | Gln | Glu | Met | Pro | Met | Gly | Arg | Thr | Ile | Leu | Lys |  |
|  |  | 1025 |  |  |  |  | 1030 |  |  |  |  | 1035 |  |  |  |  |
| gtc | acc | cca | gaa | aaa | cag | act | gtt | cca | act | cca | gta | cgg | aaa | tac | aac | 3168 |

| | | |
|---|---|---|
| Val Thr Pro Glu Lys Gln Thr Val Pro Thr Pro Val Arg Lys Tyr Asn<br>　　　1040　　　　　　　　1045　　　　　　　　1050 | | |
| tcc aat gcc aat atc ata acc aca gag gac aat aaa att cac att cac<br>Ser Asn Ala Asn Ile Ile Thr Thr Glu Asp Asn Lys Ile His Ile His<br>1055　　　　　　　　1060　　　　　　　　1065　　　　　　　　1070 | | 3216 |
| tta ggg tct cag ttt aaa cgg tcc cct ggg act tca ggt gaa gga gtc<br>Leu Gly Ser Gln Phe Lys Arg Ser Pro Gly Thr Ser Gly Glu Gly Val<br>　　　　　　　　1075　　　　　　　　1080　　　　　　　　1085 | | 3264 |
| agt cca gtt att act gtc cga cca gta aac gtg aca gcc gaa aag gag<br>Ser Pro Val Ile Thr Val Arg Pro Val Asn Val Thr Ala Glu Lys Glu<br>　　　1090　　　　　　　　1095　　　　　　　　1100 | | 3312 |
| gtt tcc acc ggc act gtc ctt cgc tct ccc agg aat cac ctc tcc tca<br>Val Ser Thr Gly Thr Val Leu Arg Ser Pro Arg Asn His Leu Ser Ser<br>1105　　　　　　　　1110　　　　　　　　1115 | | 3360 |
| cgg cct ggt gca agc aaa gtg acg agc act atc acc ata aca ccg gtc<br>Arg Pro Gly Ala Ser Lys Val Thr Ser Thr Ile Thr Ile Thr Pro Val<br>　　　1120　　　　　　　　1125　　　　　　　　1130 | | 3408 |
| aca acg tca tct gct cga gga acc cag tca gtg tca gga caa gac ggg<br>Thr Thr Ser Ser Ala Arg Gly Thr Gln Ser Val Ser Gly Gln Asp Gly<br>1135　　　　　　　　1140　　　　　　　　1145　　　　　　　　1150 | | 3456 |
| tca tcc cag cgg cct aca ccc acc cgc att cct atg tca aaa ggt atg<br>Ser Ser Gln Arg Pro Thr Pro Thr Arg Ile Pro Met Ser Lys Gly Met<br>　　　　　　　　1155　　　　　　　　1160　　　　　　　　1165 | | 3504 |
| aaa gca gga aag cca gta gtg gca gcc cca gga gca gga aat ctg acc<br>Lys Ala Gly Lys Pro Val Val Ala Ala Pro Gly Ala Gly Asn Leu Thr<br>　　　1170　　　　　　　　1175　　　　　　　　1180 | | 3552 |
| aaa ttc gag cct cga gct gag act cag tct atg aaa ata gag ctg aag<br>Lys Phe Glu Pro Arg Ala Glu Thr Gln Ser Met Lys Ile Glu Leu Lys<br>1185　　　　　　　　1190　　　　　　　　1195 | | 3600 |
| aaa tct gca gcc agc agc acc acc tct ctc gga ggg ggg aag ggc<br>Lys Ser Ala Ala Ser Ser Thr Thr Ser Leu Gly Gly Gly Lys Gly<br>　　　1200　　　　　　　　1205　　　　　　　　1210 | | 3645 |
| tgagggcagt ggctaagggg gtatgttgtg cagatgctac tgctgccgtg aaagtgaacc | | 3705 |
| ttcatctgtt tgtgccagtt ctttacatgt actaatttaa gttttaaata ttgtgtttat | | 3765 |
| aaaataacca actaataacc atttgtcttt cccattttgt gcatttgttt tgatgctggg | | 3825 |
| gaacaaaatt agcaaaacta ttgcttgctg cctagaagcc agggcgtggt ttctagttcc | | 3885 |
| agttttgctt ctagcaagtg gacccatcaa tagacccatc tgagcctgtt tcctcatcag | | 3945 |
| ttagatgtgg ggactcaatc acacgctctt caagtccggc tcccatattt cctaattgca | | 4005 |
| agccaaattt aatgtacctt gttccacaat aatttttat taaaaaaatc ctattacaaa | | 4065 |
| ataagacata ctttaactat tgtcatttgc ctctttcaca tcatgaattt gctttatgtg | | 4125 |
| ctggaaaaaa catcacatag ctatcacagg gcctggacct ctaaaatttt gcaaaaacaa | | 4185 |
| aaggttctaa gatgatttca ggaaataatg tgaacatgta ataaaatgga aatgaaatat | | 4245 |
| gg | | 4247 |

<210> SEQ ID NO 6
<211> LENGTH: 1213
<212> TYPE: PRT
<213> ORGANISM: Homo sapiens

<400> SEQUENCE: 6

Met Arg Ser Arg Asn Gln Gly Gly Glu Ser Ala Ser Asp Gly His Ile
1               5                   10                  15

Ser Cys Pro Lys Pro Ser Ile Ile Gly Asn Ala Gly Glu Lys Ser Leu
            20                  25                  30

```
Ser Glu Asp Ala Lys Lys Lys Lys Ser Asn Arg Lys Glu Asp Asp
         35                  40                  45

Val Met Ala Ser Gly Thr Val Lys Arg His Leu Lys Thr Ser Gly Glu
 50                  55                  60

Cys Glu Arg Lys Thr Lys Lys Ser Leu Glu Leu Ser Lys Glu Asp Leu
 65                  70                  75                  80

Ile Gln Leu Leu Ser Ile Met Glu Gly Glu Leu Gln Ala Arg Glu Asp
                 85                  90                  95

Val Ile His Met Leu Lys Thr Glu Lys Thr Lys Pro Glu Val Leu Glu
                100                 105                 110

Ala His Tyr Gly Ser Ala Glu Pro Glu Lys Val Leu Arg Val Leu His
             115                 120                 125

Arg Asp Ala Ile Leu Ala Gln Glu Lys Ser Ile Gly Glu Asp Val Tyr
130                 135                 140

Glu Lys Pro Ile Ser Glu Leu Asp Arg Leu Glu Glu Lys Gln Lys Glu
145                 150                 155                 160

Thr Tyr Arg Arg Met Leu Glu Gln Leu Leu Leu Ala Glu Lys Cys His
                165                 170                 175

Arg Arg Thr Val Tyr Glu Leu Glu Asn Glu Lys His Lys His Thr Asp
            180                 185                 190

Tyr Met Asn Lys Ser Asp Asp Phe Thr Asn Leu Leu Glu Gln Glu Arg
        195                 200                 205

Glu Arg Leu Lys Lys Leu Leu Glu Gln Glu Lys Ala Tyr Gln Ala Arg
    210                 215                 220

Lys Glu Lys Glu Asn Ala Lys Arg Leu Asn Lys Leu Arg Asp Glu Leu
225                 230                 235                 240

Val Lys Leu Lys Ser Phe Ala Leu Met Leu Val Asp Glu Arg Gln Met
                245                 250                 255

His Ile Glu Gln Leu Gly Leu Gln Ser Gln Lys Val Gln Asp Leu Thr
            260                 265                 270

Gln Lys Leu Arg Glu Glu Glu Lys Leu Lys Ala Ile Thr Ser Lys
        275                 280                 285

Ser Lys Glu Asp Arg Gln Lys Leu Leu Lys Leu Glu Val Asp Phe Glu
    290                 295                 300

His Lys Ala Ser Arg Phe Ser Gln Glu His Glu Glu Met Asn Ala Lys
305                 310                 315                 320

Leu Ala Asn Gln Glu Ser His Asn Arg Gln Leu Arg Leu Lys Leu Val
                325                 330                 335

Gly Leu Thr Gln Arg Ile Glu Glu Leu Glu Glu Thr Asn Lys Asn Leu
            340                 345                 350

Gln Lys Ala Glu Glu Glu Leu Gln Glu Leu Arg Asp Lys Ile Ala Lys
        355                 360                 365

Gly Glu Cys Gly Asn Ser Ser Leu Met Ala Glu Val Glu Asn Leu Arg
    370                 375                 380

Lys Arg Val Leu Glu Met Glu Gly Lys Asp Glu Glu Ile Thr Lys Thr
385                 390                 395                 400

Glu Ser Gln Cys Arg Glu Leu Arg Lys Lys Leu Gln Glu Glu His
                405                 410                 415

His Ser Lys Glu Leu Arg Leu Glu Val Glu Lys Leu Gln Lys Arg Met
            420                 425                 430

Ser Glu Leu Glu Lys Leu Glu Glu Ala Phe Ser Lys Ser Lys Ser Glu
        435                 440                 445

Cys Thr Gln Leu His Leu Asn Leu Glu Lys Glu Lys Asn Leu Thr Lys
```

-continued

```
            450                 455                 460
Asp Leu Leu Asn Glu Leu Glu Val Val Lys Ser Arg Val Lys Glu Leu
465                 470                 475                 480
Glu Cys Ser Glu Ser Arg Leu Glu Lys Ala Glu Leu Ser Leu Lys Asp
                485                 490                 495
Asp Leu Thr Lys Leu Lys Ser Phe Thr Val Met Leu Val Asp Glu Arg
                500                 505                 510
Lys Asn Met Met Glu Lys Ile Lys Gln Glu Glu Arg Lys Val Asp Gly
                515                 520                 525
Leu Asn Lys Asn Phe Lys Val Glu Gln Gly Lys Val Met Asp Val Thr
                530                 535                 540
Glu Lys Leu Ile Glu Glu Ser Lys Lys Leu Leu Lys Leu Lys Ser Glu
545                 550                 555                 560
Met Glu Glu Lys Val Tyr Asn Leu Thr Arg Glu Arg Asp Glu Leu Ile
                565                 570                 575
Gly Lys Leu Lys Ser Glu Glu Lys Ser Ser Glu Leu Ser Cys Ser
                580                 585                 590
Val Asp Leu Leu Lys Lys Arg Leu Asp Gly Ile Glu Glu Val Glu Arg
                595                 600                 605
Glu Ile Thr Arg Gly Arg Ser Arg Lys Gly Ser Glu Leu Thr Cys Pro
                610                 615                 620
Glu Asp Asn Lys Ile Lys Glu Leu Thr Leu Glu Ile Glu Arg Leu Lys
625                 630                 635                 640
Lys Arg Leu Gln Gln Leu Glu Val Val Glu Gly Asp Leu Met Lys Thr
                645                 650                 655
Glu Asp Glu Tyr Asp Gln Leu Glu Gln Lys Phe Arg Thr Glu Gln Asp
                660                 665                 670
Lys Ala Asn Phe Leu Ser Gln Gln Leu Glu Glu Ile Lys His Gln Ile
                675                 680                 685
Ala Lys Asn Lys Ala Ile Glu Lys Gly Glu Val Val Ser Gln Glu Ala
                690                 695                 700
Glu Leu Arg His Arg Phe Arg Leu Glu Glu Ala Lys Ser Arg Asp Leu
705                 710                 715                 720
Lys Ala Glu Val Gln Ala Leu Lys Glu Lys Ile His Glu Leu Met Asn
                725                 730                 735
Lys Glu Asp Gln Leu Ser Gln Leu Gln Val Asp Tyr Ser Val Leu Gln
                740                 745                 750
Gln Arg Phe Met Glu Glu Asn Lys Asn Lys Asn Met Gly Gln Glu
                755                 760                 765
Val Leu Asn Leu Thr Lys Glu Leu Glu Leu Ser Lys Arg Tyr Ser Arg
770                 775                 780
Ala Leu Arg Pro Ser Val Asn Gly Arg Arg Met Val Asp Val Pro Val
785                 790                 795                 800
Thr Ser Thr Gly Val Gln Thr Asp Ala Val Ser Gly Glu Ala Ala Glu
                805                 810                 815
Glu Glu Thr Pro Ala Val Phe Ile Arg Lys Ser Phe Gln Glu Glu Asn
                820                 825                 830
His Ile Met Ser Asn Leu Arg Gln Val Gly Leu Lys Lys Pro Val Glu
                835                 840                 845
Arg Ser Ser Val Leu Asp Arg Tyr Pro Pro Ala Ala Asn Glu Leu Thr
                850                 855                 860
Met Arg Lys Ser Trp Ile Pro Trp Met Arg Lys Arg Glu Asn Gly Pro
865                 870                 875                 880
```

```
Ser Ile Thr Gln Glu Lys Gly Pro Arg Thr Asn Ser Ser Pro Gly His
            885                 890                 895

Pro Gly Glu Val Val Leu Ser Pro Lys Gln Gly Gln Pro Leu His Ile
            900                 905                 910

Arg Val Thr Pro Asp His Glu Asn Ser Thr Ala Thr Leu Glu Ile Thr
            915                 920                 925

Ser Pro Thr Ser Glu Glu Phe Phe Ser Ser Thr Thr Val Ile Pro Thr
            930                 935                 940

Leu Gly Asn Gln Lys Pro Arg Ile Thr Ile Ile Pro Ser Pro Asn Val
945                 950                 955                 960

Met Pro Gln Lys Gln Lys Ser Gly Asp Thr Thr Leu Gly Pro Glu Arg
            965                 970                 975

Ala Met Ser Pro Val Thr Ile Thr Thr Phe Ser Arg Glu Lys Thr Pro
            980                 985                 990

Glu Ser Gly Arg Gly Ala Phe Ala Asp Arg Pro Thr Ser Pro Ile Gln
            995                 1000                1005

Ile Met Thr Val Ser Thr Ser Ala Ala Pro Ala Glu Ile Ala Val Ser
    1010                1015                1020

Pro Glu Ser Gln Glu Met Pro Met Gly Arg Thr Ile Leu Lys Val Thr
1025                1030                1035                1040

Pro Glu Lys Gln Thr Val Pro Thr Pro Val Arg Lys Tyr Asn Ser Asn
            1045                1050                1055

Ala Asn Ile Ile Thr Thr Glu Asp Asn Lys Ile His Ile His Leu Gly
            1060                1065                1070

Ser Gln Phe Lys Arg Ser Pro Gly Thr Ser Gly Glu Gly Val Ser Pro
            1075                1080                1085

Val Ile Thr Val Arg Pro Val Asn Val Thr Ala Glu Lys Glu Val Ser
            1090                1095                1100

Thr Gly Thr Val Leu Arg Ser Pro Arg Asn His Leu Ser Ser Arg Pro
1105                1110                1115                1120

Gly Ala Ser Lys Val Thr Ser Thr Ile Thr Ile Thr Pro Val Thr Thr
            1125                1130                1135

Ser Ser Ala Arg Gly Thr Gln Ser Val Ser Gly Gln Asp Gly Ser Ser
            1140                1145                1150

Gln Arg Pro Thr Pro Thr Arg Ile Pro Met Ser Lys Gly Met Lys Ala
            1155                1160                1165

Gly Lys Pro Val Val Ala Ala Pro Gly Ala Gly Asn Leu Thr Lys Phe
            1170                1175                1180

Glu Pro Arg Ala Glu Thr Gln Ser Met Lys Ile Glu Leu Lys Lys Ser
1185                1190                1195                1200

Ala Ala Ser Ser Thr Thr Ser Leu Gly Gly Gly Lys Gly
            1205                1210
```